United States Patent [19]

Garland et al.

[11] Patent Number: 5,481,021

[45] Date of Patent: Jan. 2, 1996

[54] PHENYL AMIDINES DERIVATIVES USEFUL AS PLATELET AGGREGATION INHIBITORS

[75] Inventors: Robert B. Garland, Northbrook, Ill.; Masateru Miyano, Salem, S.C.; Jeffery A. Zablocki, Mt. Prospect; Lori A. Schretzman, Gurnee, both of Ill.

[73] Assignee: G. D. Searle & Co., Chicago, Ill.

[21] Appl. No.: 90,127

[22] PCT Filed: Mar. 5, 1992

[86] PCT No.: PCT/US92/01531

§ 371 Date: Nov. 19, 1993

§ 102(e) Date: Nov. 19, 1993

[87] PCT Pub. No.: WO92/15607

PCT Pub. Date: Sep. 17, 1992

Related U.S. Application Data

[63] Continuation-in-part of Ser. No. 665,119, Mar. 6, 1991, abandoned.

[51] Int. Cl.⁶ .................................................. C07C 229/36
[52] U.S. Cl. .............................. 560/35; 548/507; 549/58; 549/407; 549/467; 562/440
[58] Field of Search ........................ 562/440; 560/35; 514/533, 563, 415, 443, 456, 469; 548/507; 549/58, 407, 467

[56] References Cited

U.S. PATENT DOCUMENTS

| | | | |
|---|---|---|---|
| 4,517,686 | 5/1985 | Ruoslahti et al. ........................ | 3/1 |
| 4,578,079 | 3/1986 | Ruoslahti et al. ........................ | 623/11 |
| 4,589,881 | 5/1986 | Pierschbacher et al. ................. | 623/11 |
| 4,614,517 | 9/1986 | Ruoslahti et al. ........................ | 623/11 |
| 4,661,111 | 4/1987 | Ruoslahti et al. ........................ | 623/11 |
| 4,683,291 | 7/1987 | Zimmerman et al. ................... | 530/324 |
| 4,857,508 | 8/1989 | Adams et al. ............................ | 514/18 |
| 4,879,313 | 11/1989 | Tjoeng et al. ............................ | 514/616 |

FOREIGN PATENT DOCUMENTS

| | | | |
|---|---|---|---|
| 0275748 | 7/1988 | European Pat. Off. .......... | C07K 7/06 |
| 0298820 | 1/1989 | European Pat. Off. .......... | C07K 7/06 |
| 0372486 | 6/1990 | European Pat. Off. ....... | C07C 279/14 |
| 384362 | 8/1990 | European Pat. Off. .......... | C07K 5/10 |
| 0381033 | 8/1990 | European Pat. Off. ....... | C07C 311/19 |
| 0410540 | 1/1991 | European Pat. Off. .......... | C07K 7/06 |

OTHER PUBLICATIONS

Kloczewiak, et al. *Biochem.*, 23, 1767–1774 (1984).
Ruggeri, et al. *Proc. Natl. Acad. Sci.*, 83, 5708–5712 (1986).
Plow, et al. *Proc. Natl. Acad. Sci.*, 82, 8057–8061 (1985).
Ginsberg, et al. *J. Biol. Chem.*, 260, (7), 3931–3936 (1985).
Haverstick, et al. *Blood*, 66, (4), 946–952 (1985).
Ruoslahti and Pierschbacher *Science*, 238, 491–497 (1987).

*Primary Examiner*—José G. Dees
*Assistant Examiner*—Barbara S. Frazier
*Attorney, Agent, or Firm*—Joy A. Serauskas; Roger A. Williams

[57] ABSTRACT

This invention relates to phenyl amidine derivatives having the following formula

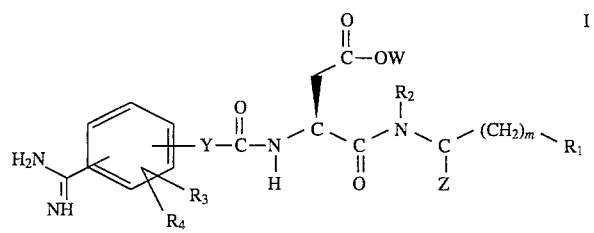

or a pharmaceutically acceptable salt which are useful in the inhibition of platelet aggregation. This invention also relates to pharmaceutical compositions of such phenyl amidine derivatives.

44 Claims, No Drawings

PHENYL AMIDINES DERIVATIVES USEFUL AS PLATELET AGGREGATION INHIBITORS

This application is a 371 of PCT/US92/01531, filed Mar. 5, 1992, and a continuation-in-part of U.S. Ser. No. 07/665,119, filed Mar. 6, 1991 now abandoned.

FIELD OF THE INVENTION

This invention is in the field of mammalian therapeutics and relates to compounds for the treatment of mammalian disorders such as cardiovascular disorders. Of particular interest is a class of phenyl amidines derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

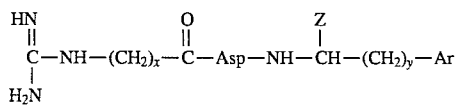

wherein x=6 to 10, y=0 to 4,

Z=H, COOH, $CONH_2$ OR $C_{1-6}$ alkyl,

Ar=phenyl, biphenyl or naphthyl, each substituted with 1 to 3 methoxy groups, or an unsubstituted phenyl, biphenyl, naphthyl, pyridyl or thienyl group, and Asp=aspartic acid residue.

U.S. Pat. No. 4,977,168 discloses compounds having the following structural formula

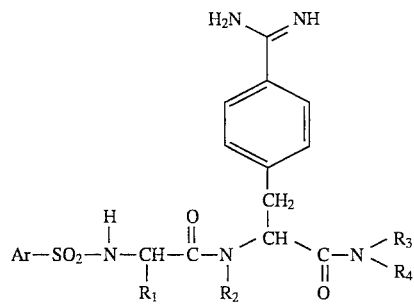

wherein $R_1$ represents hydrogen, a lower alkyl group, a lower hydroxyalkyl group, a benzyl group, a phenyl group or a 4-hydroxyphenyl group;

$R_2$ represents a lower alkyl, lower alkenyl, lower alkynyl or benzyl group, or a lower alkoxycarbonylalkyl, lower carboxyalkyl, or lower hydroxyalkyl group;

$R_3$ and $R_4$ identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents. These compounds are structural distinct from the present invention because they are arylsulphonylaminoacyl aminophenylalaninamide derivatives in contrast to the compounds of the present invention which are alkanoic acid/esters-1-amidinophenylalkyl carbonylamino derivatives.

U.S. Pat. No. 4,791,102 discloses compounds having the following structural formula

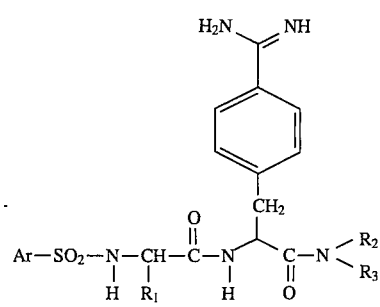

wherein
- $R_1$ represents a lower alkyl, lower hydroxyalkyl, or benzyl group, a phenyl or a 4-hydroxyphenyl group.
- $R_2$ and $R_3$ identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.
- Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics. These compounds are structural distinct from the present invention because they are arylsulphonylaminoacylaminophenyl alaninamides in contrast to the compounds of the present invention which are alkanoic acid/esters-1-amidinophenylalkylcarbonyl amino derivatives.

European Patent Application 372,486 discloses N-acyl beta amino acid derivatives of the formula:

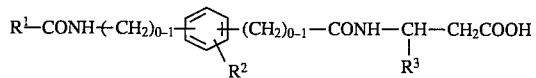

and their salts. Said compounds are useful for inhibiting platelet aggregation in the treatment of thrombosis, stroke, myocardial infarction, inflammation and arteriosclerosis, and for inhibiting metastasis.

European Patent Application 381 033 A1 discloses amidino or guanidino-aryl substituted alkanoic acid derivatives having the following structural formula

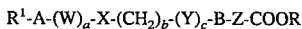

which are useful for the treatment of thrombosis, apoplexy, cardiac infarction, inflammation, arteriosclerosis and tumors. These compounds are structural distinct from the present invention because they are aryl acetic acid/esters 2-amidino/guanidino phenylalkylcarbonyl amino derivatives in contrast to the compounds of the present invention which are alkanoic acid/esters-1-amidinophenylalkylcarbonyl amino derivatives.

European Patent Application 445,796 A2 discloses acetic acid derivatives having the formula

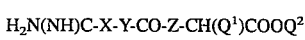

(Formula A)

where
- $Q^1$ stands for hydrogen, methyl or phenyl,
- $Q^2$ stands for hydrogen, phenyl-low-alkyl or low alkyl that can be cleaved under physiological conditions,
- X stands for 1,4-phenylene, 2,5- or 3,6-pyridylene or, 1,4-piperidinylene, which is bonded to group Y through the C atom in the 4-position,
- Y is a group having the formula

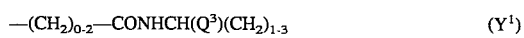 (Y¹)

 (Y²)

 (Y³)

 (Y⁴)

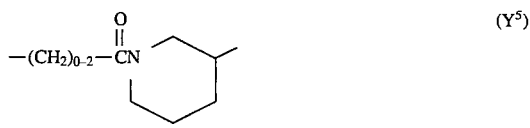 (Y⁵)

 (Y⁶)

OR

 (Y⁷)

where
- $Q^3$ stands for hydrogen, methyl, phenyl, —COOH, —COO— low-alkyl, —CONH(CH$_2$)$_2$—COOH or —CONH(CH$_2$)$_2$—COO-low-alkyl,
- $Q^4$ hydrogen, methyl or phenyl,
- Z a 1,4-piperazinylene group, a 1,4-piperazinylene group which is bonded to the CO group through the N atom in the 1-position or a group having the formula

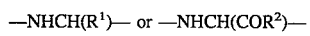

where
- $R^1$ stands for hydrogen, methyl, phenyl or a —COO-low-alkyl,
- $R^2$ stands for the residue of an α-aminocarboxylic acid bonded through the amino group or of an ester or amide thereof, or a group having the formula —NHCH$_2$CH$_2$—Ar, or —CO-R$^2$, or, if applicable, a mono- or di-low-alkylated carbamoyl group or a pyrrolidinoyl or piperidinoyl group,
- Ar stands for a phenyl or a phenyl substituted by low alkyl, low alkoxy, —COOH, —COO-low-alkyl, —O(CH$_2$)$_{1-4}$—COOH, —O(CH$_2$)$_{1-4}$—COO-low-alkyl, —CONH$_2$, —CONH-low-alkyl, —CON(low alkyl)$_2$, pyrrolidinoyl or piperidinoyl which are said to have inhibitory action on the bonding of adhesive proteins to blood platelets as well as blood platelet aggregation and cell-cell adhesion. These compounds are structurally distinct from the present invention because they have an additional —NHCH(R$^1$) or —NHCH(COR$^2$)— or a piperazinylene group at the "Z" position of Formula A. An additional —NHCH(R$^1$) or an additional —NHCH(COR$^2$) or a piperazinylene group is not present in the instant invention.

SUMMARY OF THE INVENTION

The present invention relates to a class of compounds represented by the formula:

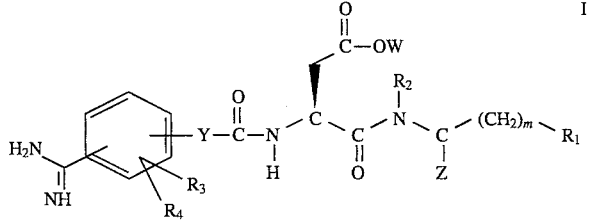

or a pharmaceutically acceptable salt thereof, wherein $R_1$ is selected from phenyl; substituted phenyl wherein each substituent can be selected from the group consisting of alkyl having 1 to 6 carbon atoms, halo, alkoxy having 1 to 6 carbon atoms, trifluoromethyl, hydroxy and carboxyl; alkyl having 1 to 6 carbon atoms wherein said alkyl may be substituted by alkyl having 1 to 4 carbon atoms; carboxyl; and a fully unsaturated heteromonocyclic ring structure having 5 or 6 ring carbon atoms wherein 1 of the ring carbon atoms is replaced by nitrogen, oxygen or sulfur and wherein said heteromonocyclic ring is fused to a benzene ring;

$R_2$ is hydrido; alkyl having 1 to 6 carbon atoms; phenyl; phenylalkyl wherein the alkyl is 1 to 6 carbon atoms and wherein the phenyl ring may be independently substituted one or more times by a substituent selected from alkyl having 1 to 6 carbon atoms, halo, and alkoxy having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms; alkynyl having 2 to 6 carbon atoms or alkylcarbonylaminoalkyl wherein the alkyl has 1 to 6 carbon atoms and wherein the amino may be further substituted by alkyl having 1 to 4 carbon atoms;

Z is hydrido, carboxyl, alkoxycarbonyl having 1 to 6 carbon atoms or alkylcarboxyl having 1 to 6 carbon atoms; and m is an integer from 0 to 4.

The invention further relates to pharmaceutical compositions comprising a compound of formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

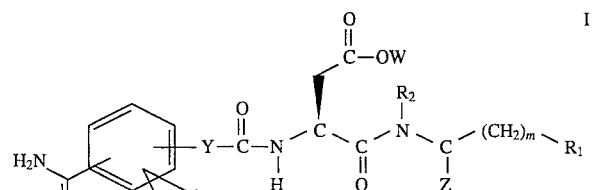

or a pharmaceutically acceptable salt thereof, $R_1$ is selected from phenyl or substituted phenyl wherein each substituent can be selected from the group consisting of alkyl having 1 to 6 carbon atoms, halo, alkoxy having 1 to 6 carbon atoms, trifluoromethyl, hydroxy and carboxyl;

$R_2$ is hydrido or alkyl having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

Exemplifying this embodiment are the following compounds:

N-[N-[5-[4-(aminoiminomethyl)phenyl]-1-oxopentyl]-L-α-aspartyl]-L-phenylalanine, dimethyl ester;

N-[N-[5-[4-(aminoiminomethyl]phenyl]-1-oxopentyl]-L-α-aspartyl]-L-phenylalanine, diethyl ester;

N-[N-[5-[4-(aminoiminomethyl)phenyl]-1-oxopentyl]-L-α-aspartyl]-L-phenylalanine;

N-[N-[5-[4-(aminoiminomethyl)phenyl]-1-oxopentyl]-L-α-aspartyl]-L-phenylalanine acetate;

N-[N-[5-[3-(aminoiminomethyl)phenyl]-1-oxopentyl]-L-α-aspartyl]-L-phenylalanine;

N-[N-[5-[4-(aminoiminomethyl)phenyl]-1-oxo-4-pentynyl]-L-α-aspartyl]-L-phenylalanine;

N-[N-[5-[4-(aminoiminomethyl)phenyl]-1-oxo-4E-pentenyl]-L-α-aspartyl]-L-phenylalanine;

N-[N-[5-[4-(aminoiminomethyl)phenyl]-1-oxo-4Z-pentenyl]-L-α-aspartyl]-L-phenylalanine;

N-[N-[5-[4-(aminoiminomethyl)phenyl]-1-oxopentyl]-L-α-aspartyl]-N-methyl-L-phenylalanine;

N-[N-[5-[4-(aminoiminomethyl)phenyl]-1,4-dioxopentyl]-L-α-aspartyl]-L-phenylalanine;

N-[N-[6-[4-(aminoiminomethyl)phenyl]-1-oxohexyl]-L-α-aspartyl]-L-phenylalanine;

N-[N-[5-[4-(aminoiminomethyl)phenyl]-4-hydroxy-1-oxopentyl]-L-α-aspartyl]-L-phenylalanine;

N-[N-[6-[3-(aminoiminomethyl)phenyl]-1-oxo-5Z-hexenyl]-L-α-aspartyl]-L-phenylalanine;

N-[N-[4-[4-(aminoiminomethyl)phenyl]-1-oxobutyl]-L-α-aspartyl]-L-phenylalanine;

N-[N-[5-[4-(aminoiminomethyl)phenyl]-1-oxopentyl]-L-α-aspartyl]-L-phenylalanine, monohydrochloride;

3S-[[5-[4-(aminoiminomethyl)phenyl]-1-oxopentyl] amino]-4-oxo-4-[(2-phenylethyl)amino] butanoic acid, acetate;

3S-[[5-[4-(aminoiminomethyl)phenyl]-1-oxopentyl] amino]-4-[[2-(4-methoxyphenyl)ethyl] amino]-4-oxobutanoic acid; and N-[N-[6-[4-(aminoiminomethyl)phenyl]-1-oxohexyl]-L-α-aspartyl]-L-phenylalanine.

Another preferred embodiment of the present invention is a compound of the formula:

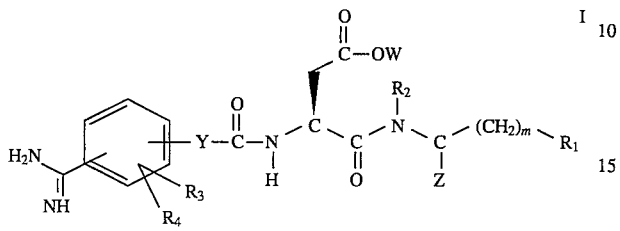

or a pharmaceutically acceptable salt thereof, $R_1$ is alkyl having 1 to 6 carbon atoms wherein said alkyl may be substituted by alkyl having 1 to 4 carbon atoms;

$R_2$ is hydrido or alkyl having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

Exemplifying this embodiment are the following compounds:

3S-[[5-[4-(aminoiminomethyl)phenyl]-1-oxopentyl] amino]-4-[(2-methylpropyl)amino]-4-oxobutanoic acid; and N-[N-[5-[4-(aminoiminomethyl)phenyl]-1-oxopentyl]-L-α-aspartyl]-L-valine A further preferred embodiment of the present invention is a compound of the formula:

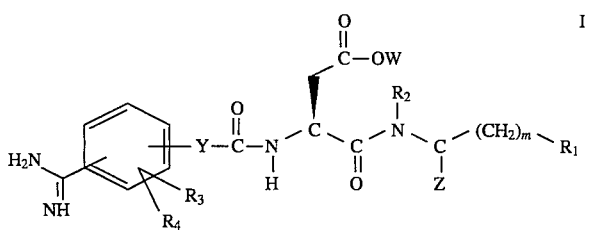

or a pharmaceutically acceptable salt thereof, $R_1$ is carboxyl;

$R_2$ is hydrido; alkyl having 1 to 6 carbon atoms; phenyl; phenylalkyl wherein the alkyl is 1 to 6 carbon atoms and wherein the phenyl ring may be independently substituted one or more times by a substituent selected from alkyl having 1 to 6 carbon atoms, halo, and alkoxy having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

Exemplifying this embodiment are the following compounds:

3 S-[[5-[4-(aminoiminomethyl)phenyl]-1-oxopentyl] amino]-4-[(2-carboxyethyl)(phenylmethyl)amino]-4-oxobutanoic acid;

3S-[[5-[4-(aminoiminomethyl)phenyl]-1-oxopentyl] amino]-4-[(2-carboxyethyl)(2-phenylethyl)amino]-4-oxobutanoic acid;

3 S-[[5-[4-(aminoiminomethyl)phenyl]-1-oxopentyl] amino]-4-[(2-carboxyethyl)[2-(4-methoxyphenyl)ethyl] amino]-4-oxobutanoic acid; and 3 S-[[5-[4-(aminoiminomethyl)phenyl]-1-oxopentyl] amino]-4-[(2-carboxyethyl)(2-methylpropyl)amino]-4-oxobutanoic acid.

As used herein, the term "hydrido" denotes a single hydrogen atom (H). This hydrido group may be attached, for example, to a oxygen atom to form a hydroxyl group; or, as another example, two hydrido groups may be attached to a carbon atom to form a —$CH_2$— group.

As used herein, the term "alkyl" either alone or within other terms such as "phenylalkyl", and "alkylcarboxyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenyloxy, 3-methylbutoxy, 1-methylbutoxy, 1-ethylpropoxy, 2-2-dimethylpropoxy, 1,1-dimethylpropoxy, hexenyloxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl- 1-butenyl, 2-methyl-2-butenyl, 2,3-dimethyl-2-butenyl and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, pentynyl, and hexynyl.

As used herein the term "halo" embraces halogen atoms. Illustrative of such atoms are chloro (Cl), fluoro (F), bromo (Br) and iodo (I).

As used herein the term "alkoxycarbonyl" represents the radical of the formula

ROCO— wherein the R represents an alkyl group. Illustrative of such radicals are methoxycarbonyl, ethoxycarbonyl, propanoxycarbonyl, pentanoxycarbonyl and hexenyloxycarbonyl.

As used herein, the term "alkylcarboxyl" represents the radical of the formula

RCOO— wherein the R represents an alkyl group. Illustrative of such groups are methylcarboxyl and ethylcarboxyl.

As used herein, the term "alkylcarbonylaminoalkyl" represents the radical of the formula

RCONHR wherein R represents an alkyl group. The amino portion of the radical RCONHR may be further substituted by alkyl having 1 to 4 carbon atoms.

As used herein the term "heteromonocyclic" embraces fully unsaturated, unsubstituted hydrocarbon radicals having 5 or 6 ring carbon atoms wherein 1 of the ring carbons is replaced by nitrogen, oxygen or sulfur and wherein said heteromonocyclic structure is fused to a unsubstituted benzene ring. Illustrative of such radicals are indolyl, benzofuranyl, benzothiophenyl and chromenyl. Attachment of the heteromonocyclic structure wherein said structure is fused to a benzene ring to the remaining portion of the molecule represented by formula I may be through a ring carbon atom of the heteromonocyclic structure.

As used herein the term "phenyl" denotes a monocyclic arene in which one hydrogen atom from a carbon atom of the ring has been removed.

Substitution to said phenyl radical can be to any available ring carbon atom.

As used herein the term "phenylalkyl" embraces a phenyl radical which is substituted by an alkyl group. Attachment of the phenylalkyl radical to the remaining portion of the molecule represented by Formula I is through the alkyl portion of the phenylalkyl radical.

The wedged bond of formula I (∇) distinguishes between the L and D configuration for the isomers and designates the L configuration at that chiral center. The L configuration is alternatively referred to as the S configuration.

While the compounds herein have an L configuration at the chiral center as shown in Formula I, other isomers can exist in the compounds of Formula I and such other isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The compounds of formula I may be prepared by methods analogous to solution phase peptide synthesis [see: The Peptides: Analysis, Synthesis, Biology (E. Gross and J. Meienhofer, eds.), Vol. 1–5, Academic Press, New York)] combined with standard synthetic methods. A general synthetic sequence is outlined in Scheme A. The amide bonds were prepared using standard coupling reagents, e.g. 1,3-dicyclohexylcarbodiimide (DCC) (Scheme A). The cyano group is converted to the amidine via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). The final compounds were obtained by purification by reverse phase high pressure liquid chromatography [High Performance Liquid Chromatography Protein and Peptide Chemistry (F. Lottspeich, A. Henscher, K. P. Hupe, eds.) Walter DeGruyter, New York, 1981].

The benzonitrile acid of Scheme A where Y= alkenyl, alkynyl, alkyl, alkyl carbonyl, or alkyl hydroxy having 2 to 4 carbon atoms can be prepared in the following manner: The halobenzonitrile ($R_3$, $R_4$=H) is coupled to an omega alkenoic or alkynoic acid using a palladium (O) based coupling reaction ["Heck Reaction"—Palladium Reagents in Organic Syntheses (Richard F. Heck), Academic Press, New York, 1985]. The preferred conditions for the palladium coupling reaction differed for the alkynoic acid and the alkenoic acid coupling components. The preferred conditions for the alkynoic acid coupling component is dependent on the Y substituent. When Y=alkynyl having 2 to 4 carbon atoms, the preferred conditions for the palladium coupling reaction utilized tetrakis(triphenylphosphine)-palladium (O) as catalyst and piperidine as the solvent [Scheme B, for related conditions see: H. A. Dieck and F. R. Heck J. Organometallic Chem. 259–263 (1975)]. When Y=alkenyl having 2 to 4 carbon atoms, the preferred conditions for the alkenoic acid coupling component utilized the phase transfer conditions of Jeffery and Larock [Scheme B, T. Jeffery J. Chem. Soc. Chem. Commun. 1287–89 (1984); R. C. Larock Tetrahedron Lett. 2603–2606 (1989)]. These conditions [phase transfer agent— tetrabutylammonium salt, catalyst-palladium (II) acetate, base-potassium acetate, solvent-dimethyl formamide] are extremely mild conditions which afforded a good yield of coupled olefin. Compounds where Y= alkyl were obtained through a selective reduction of the double bond by catalytic reduction over palladium on calcium carbonate. Interestingly, when the phase transfer conditions for Jeffery and Larock are used with the alkynoic acid coupling component an enol-lactone is isolated in good yield (Scheme C). The enol-lactone can be directly coupled to the dipeptide or dipeptide mimic by refluxing in acetonitrile to afford Y=alkyl carbonyl and alkyl hydroxy derivatives (after reduction, Scheme C). The required omega alkenoic acids are either commercially available or can be synthesized by oxidation of the omega alkenols [E. J. Corey and G. Schmidt Tetrahedron Lett. 399 (1979)]. The required omega alkynoic acids are either commercially available or can be synthesized from the omega haloalkanoic acids and lithium acetylide [W. J. DeJarlais, E. A. Emken Synthetic Commun. 653 (1980); J. Cossy, J. P. Pete Tetrahedron Lett. 573 (1986)].

An alternative method for the preparation of the (cyanophenyl)alkenoic acid unit can be employed using a standard Wittig reaction (Wittig Reaction—Recent Review—B. E. Maryanoff, A. B. Reitz Chem Rev. 863–927 (1989)] with cyanobenzaldehyde and an omega substituted (carboxyalkyl)triphenylphosphonium bromide as the two reaction components (Scheme D) [for related conditions see: J. Am. Chem. Soc., 397 (1970); Ibid 6831 and 7185 (1973)].

The substituents, $R_3$, $R_4$=halogen, alkyl, hydroxy, or alkoxy, can be introduced where Y=alkyl at the benzonitrile stage (e.g. compound 4, Scheme K) using bromine, iodine, or chlorine to halogenate the ring (Scheme E). The alkyl group can be introduced by low temperature lithium halogen exchange followed by quenching with the appropriate aldehyde [see: W. E. Parham, C. K. Bradsher Acct. Chem. Res.

300 (1982)]. The resultant alcohol can be converted to $R_3$, $R_4$=alkyl by hydrogenolysis [Reductions in Organic Chemistry (M. Hudlicky, ed.), John Wiley & Sons, New York, 1984]as shown in Scheme E. The substituents, $R_3$, $R_4$=hydroxy or alkoxy, can be introduced by low temperature lithium halogen exchange followed by quenching with the electrophilic bis(trimethylsilyl)peroxide [(TMSO)$_2$ -Scheme E) M. Taddei and A. Ricci *Synthesis* 633–635 (1986)] which affords the silyl ether. The silyl ether can be converted to the $R_3$, $R_4$=OH by treatment with hydrochloric acid [M. Taddei and A. Ricci ibid]. The $R_3$, $R_4$=OR can be formed by treating the derivative where $R_3$, $R_4$=OH with weak base ($K_2CO_3$) and an appropriate alkyl halide [$R_8$-Hal, 2 equivalents, see: C. F. H. Allen and J. W. Gates, Jr. *Organic Syntheses Coll. Vol.* 3 140 (1955)] which will form the ester as well. The ester can be selectively cleaved in the presence of the ether with one equivalent of sodium hydroxide (Scheme E).

Additional compounds, where Y=carbonyl alkyl, can be introduced at the benzonitrile stage with the following substitution for starting material, compound 4 (Scheme K): the ketoacid whose synthesis is shown in Scheme F would be used in place of compound 4. The commercially available beta ketoester can be treated with bis(2,4-pentanedionato)nickel(II), Ni(acac)2, and methyl acrylate to afford the adduct as shown in Scheme F [J. H. Nelson, P. N. Howells, G. C. DeLullo, G. L. Landen, and R. A. Henry *J. Org. Chem.* 1246–1249 (1980)]. The methyl esters can be cleaved and the beta ketoacid can be decarboxylated under the conditions given [lithium chloride-dimethyl sulfoxide, LiCl-DMSO, A. B. Holmes, C. Swithenbank, S. F. Williams *J. Chem. Soc., Chem. Commun.* 265 (1986)].

Compounds, where Y=alkylcarbonylaminoalkyl, can be introduced at the benzonitrile stage with the following substitution for starting material, compound 4 (Scheme K): the benzonitrile alkylcarbonylaminoalkyl whose synthesis is shown in Scheme G would be used in place of compound 4. The omega benzonitrile alkanoic acids are either commercially available or their preparation is known in the literature (e.g. 4-cyanohydrocinnamic acid—Schultz, E. M. U.S. Pat. No. 3,860,639). The amino acids used in the coupling are either commercially available (e.g. glycine, sarcosine, beta alanine) or readily synthesized from the omega amino acids through a reductive amination.

Compounds, where $R_2$=alkyl, phenyl or phenyl alkyl can be prepared following the general method in Scheme H. The appropriate secondary amines can be purchased or readily synthesized through a Michael reaction [Advanced Organic Chemistry (J. March, ed.), John Wiley & Sons, New York 1985] of a primary amine and tert-butyl acrylate or reductive amination [Reductions in Organic Chemistry (M. Hudlicky, ed.), John Wiley & Sons, New York, 1984] processes using the appropriate primary amine and aldehyde.

Compounds where Z=alkyl carboxyl can be prepared by homologation of commercially available amino acids using the Arndt-Eistert reaction [Meir and Zeller *Angew. Chem. Int. Ed. Eng.* 32–43 (1975); M. Rodriguez et al *Tetrahedron Lett.* 5153 (1990); W. J. Greenlee *J. Med. Chem.* 434 (1985) and references therein] or utilizing other known syntheses of homologated amino acids [e.g. phenylalanine is homologated through the addition of a malonate anion to an activated aziridine obtained from phenylalanine—Tseng, C. C., Terashima, S. and Yamada, S.-I. *Chem. Pharm. Bull.* 29–40 (1977)].

Compounds in which the benzamidine is replaced with a naphthylamidine can be prepared by substituting the cyanonaphthyl acids of Schemes I or J for the starting material 4 of Scheme K. The 6-cyano-2-naphthol can be prepared from 6-bromo-2-naphthol [T. Aoyama. et. al *Chem. Pharm. Bull.* 1458–71 (1985)]. In Scheme J, the naphthyl triflate was prepared using N-phenyltrifluoromethanesulfonamide and triethylamine [J. B. Hendrickson; R. Bergeron *Tetrahedron Lett.* 4607– 10 (1973)]. The naphthyl triflate was coupled to tert-butyl acrylate using tetrakis(triphenylphosphine)palladium (O) as catalyst and acetonitriletriethylamine as the solvent [for related conditions see: H. A. Dieck and F. R. Heck *J. Organometallic Chem.* 259–263 (1975)].

A specific synthesis of the antiplatelet agent 9 is shown in Scheme K. The compound numbers correspond to the compound numbers in example 1. Examples 2–27 were prepared using the method of example 1 with the specific changes as stated in each example, and in the general manner described in Scheme A. Examples 2–27 further illustrate the nature of the compounds in this invention. It will be understood that these compounds are not limited to the disclosed methods of making them.

The final products can be converted to alkyl esters (W=alkyl having 1 to 6 carbon atoms by treating the corresponding carboxylic acid derivatives with the appropriate alcohol under acid catalysis in the manner of Example 2.

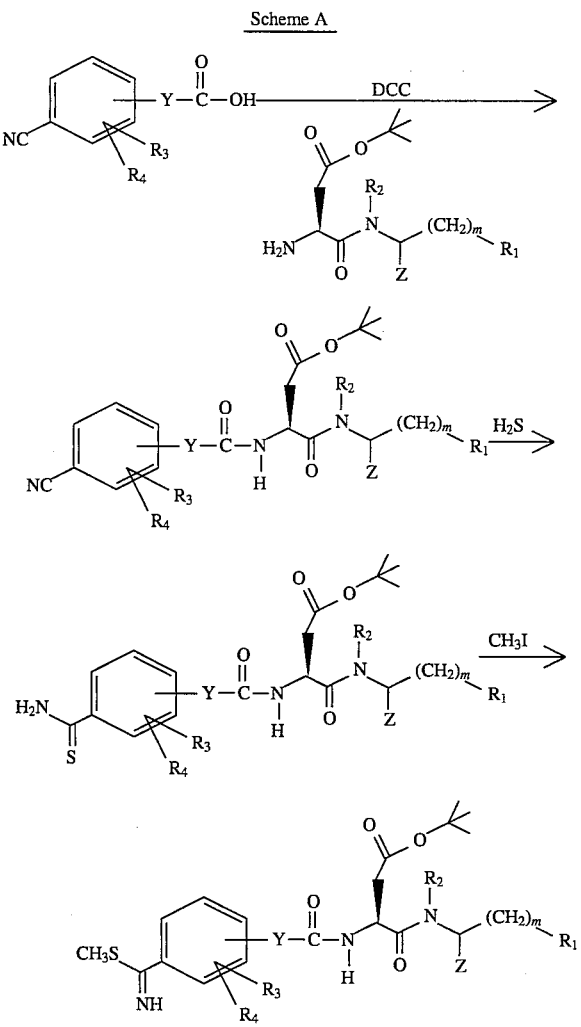

Scheme A

-continued
Scheme A
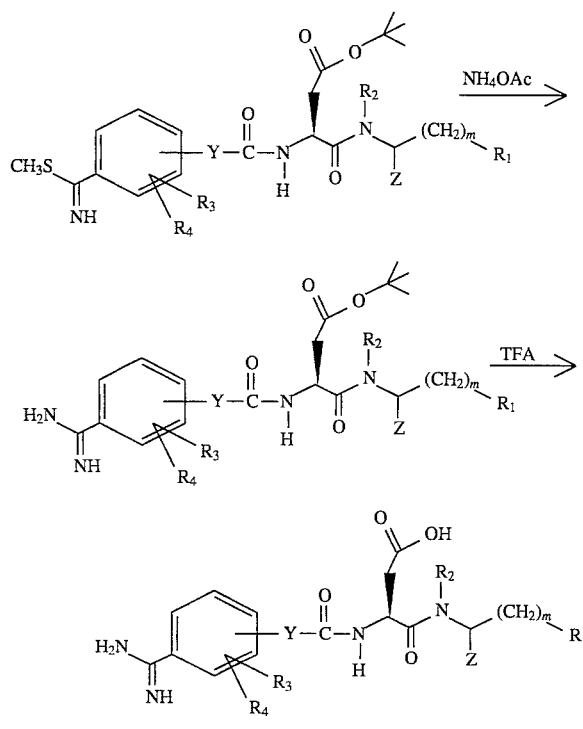
Scheme B
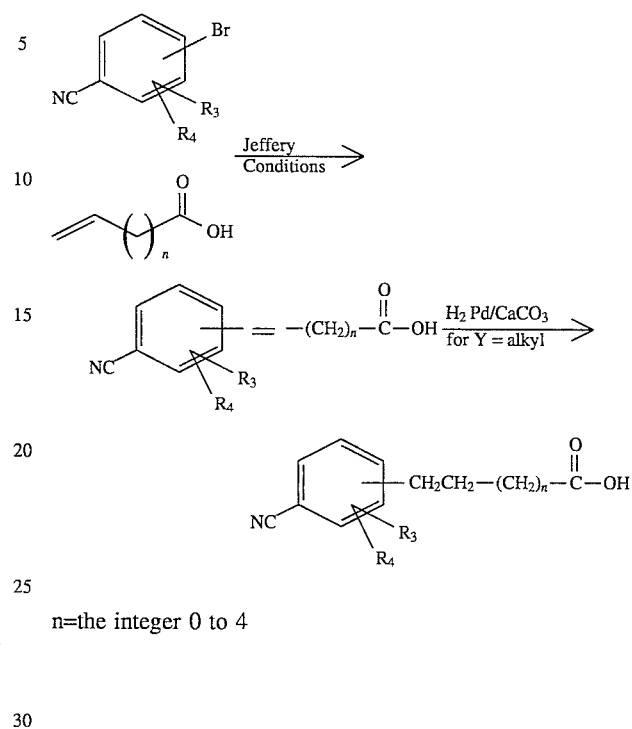
-continued
Scheme B
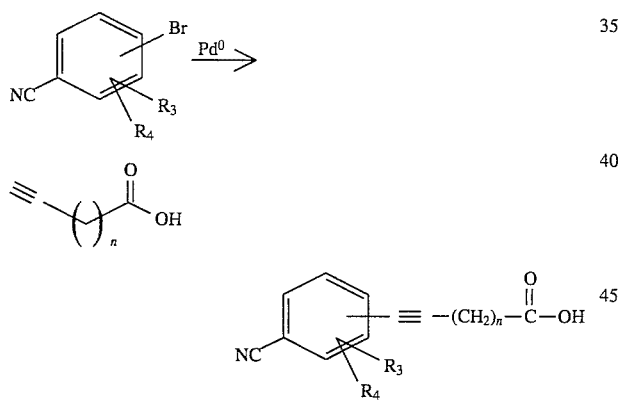
n = the integer 0 to 4

Scheme C
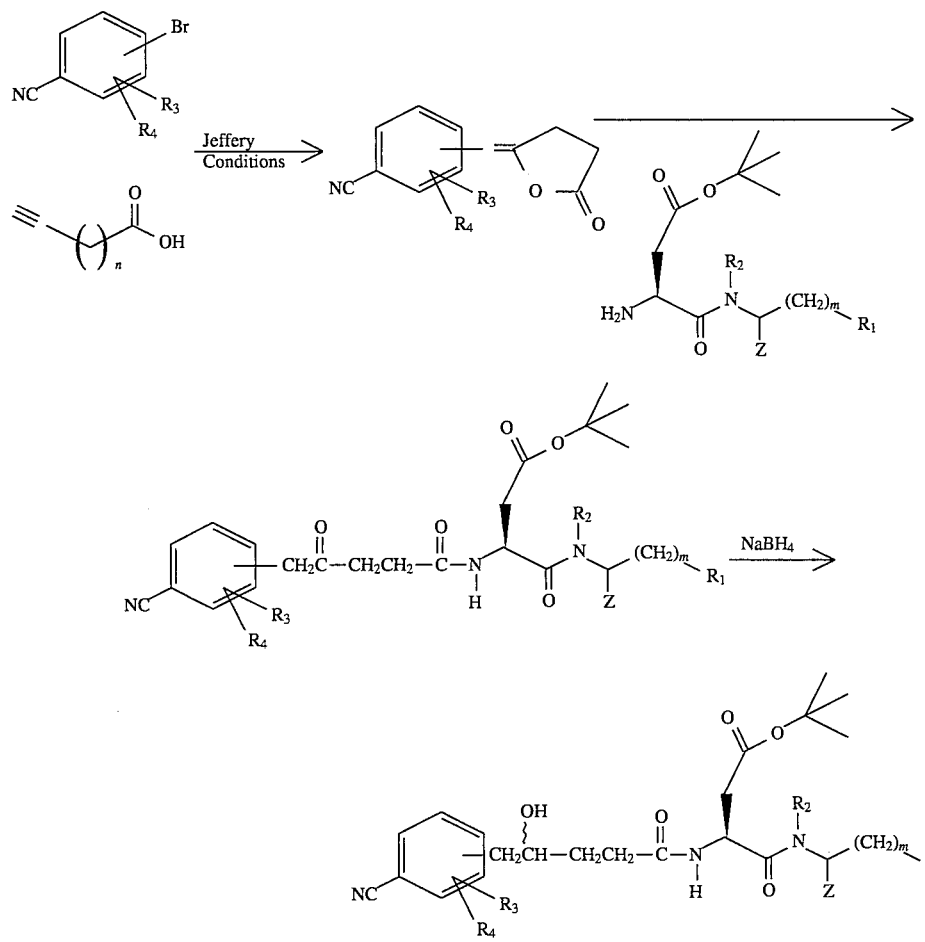
Scheme D
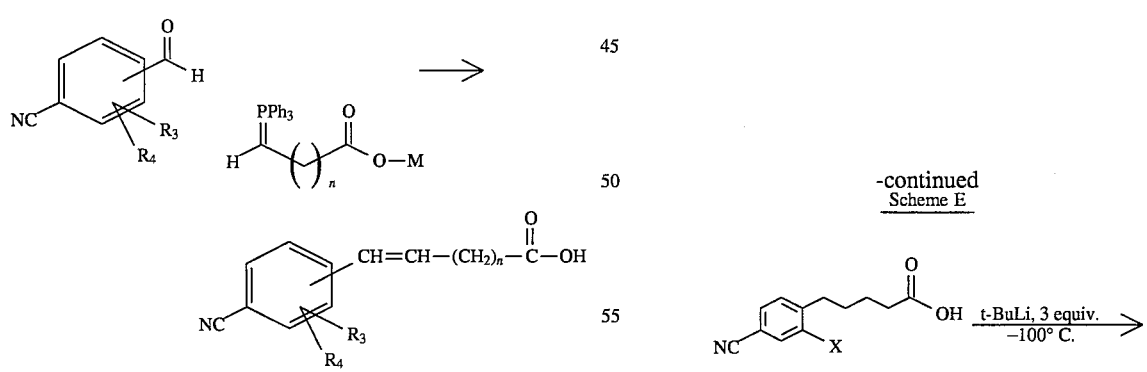
n=the integer 0 to 4
Scheme E
-continued
Scheme E -continued
Scheme E
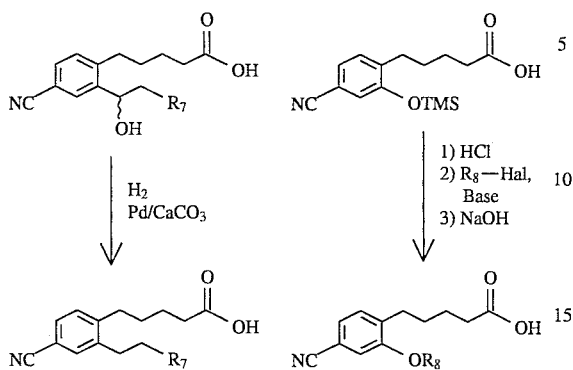
In the above scheme $R_7$ is alkyl having 1 to 4 carbon atoms and $R_8$ is alkyl having 1 to 6 carbon atoms.
Scheme F
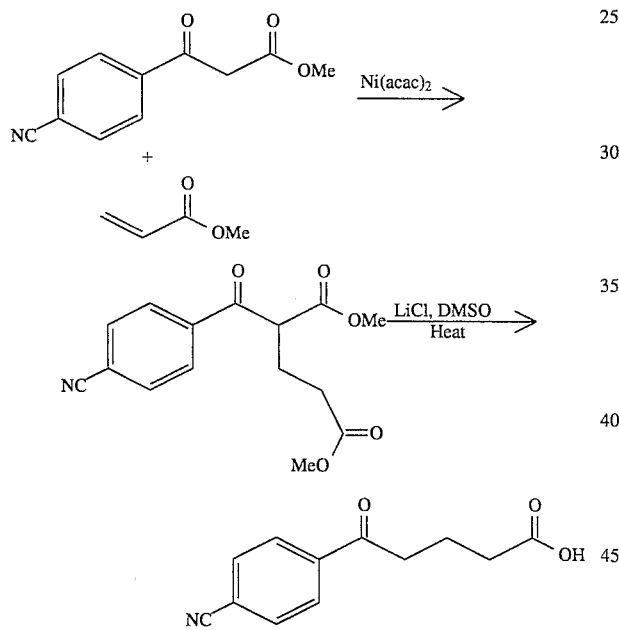
Scheme G
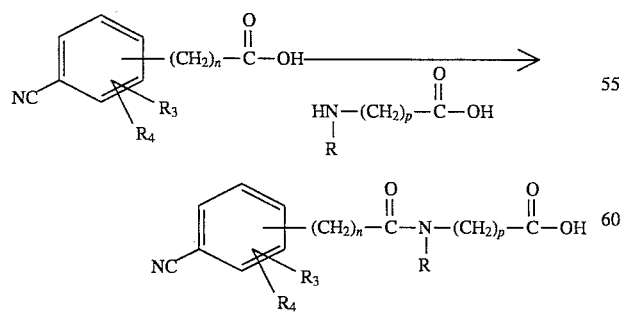
p=the integer 1 to 4
Scheme H
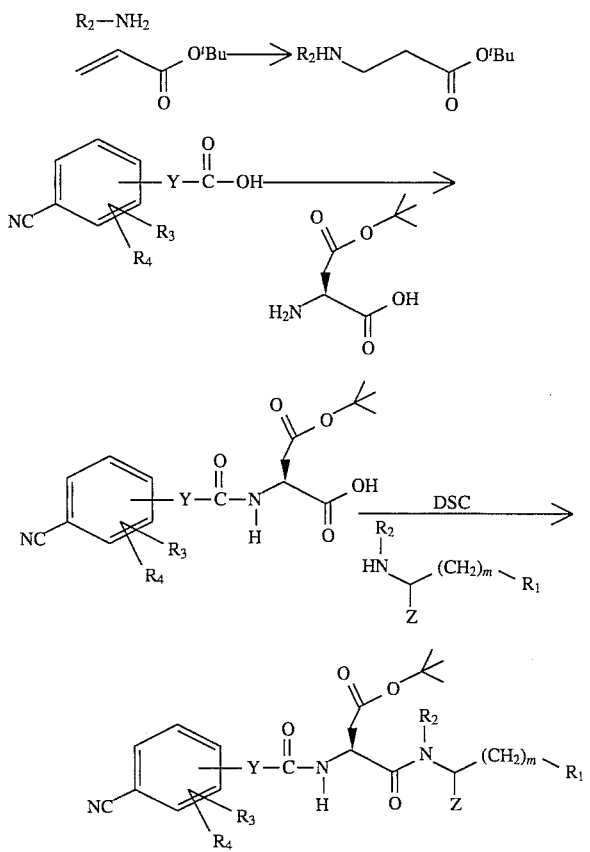
Scheme I
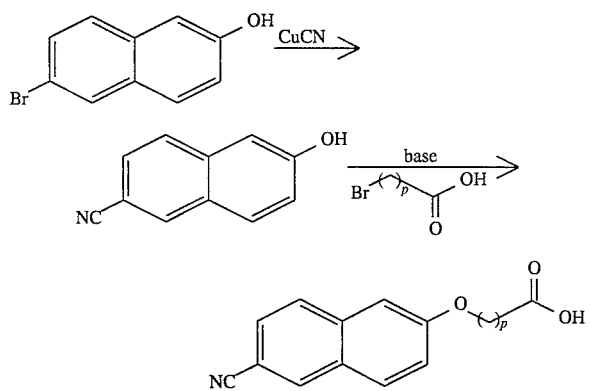
p=the integer 1 to 4
Scheme J
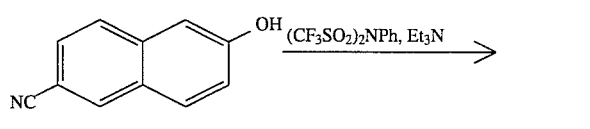

-continued
Scheme J

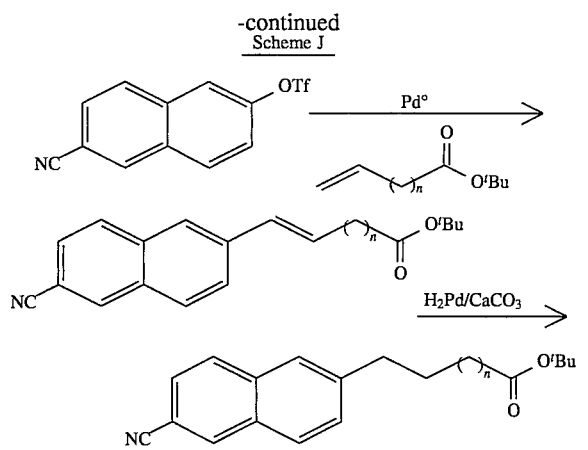

Scheme K

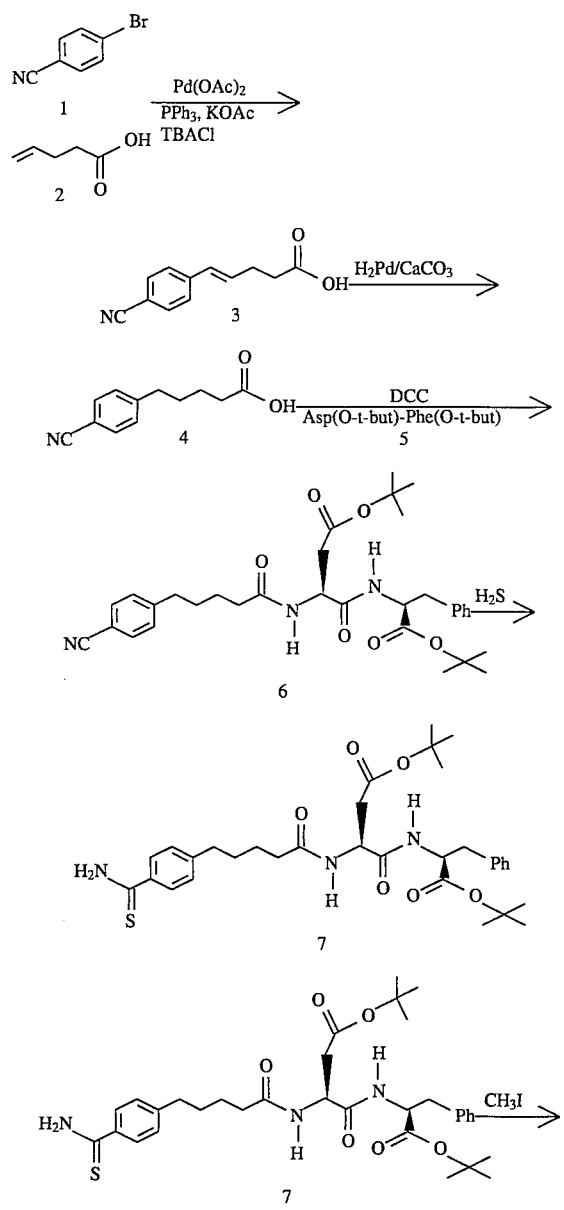

-continued
Scheme K

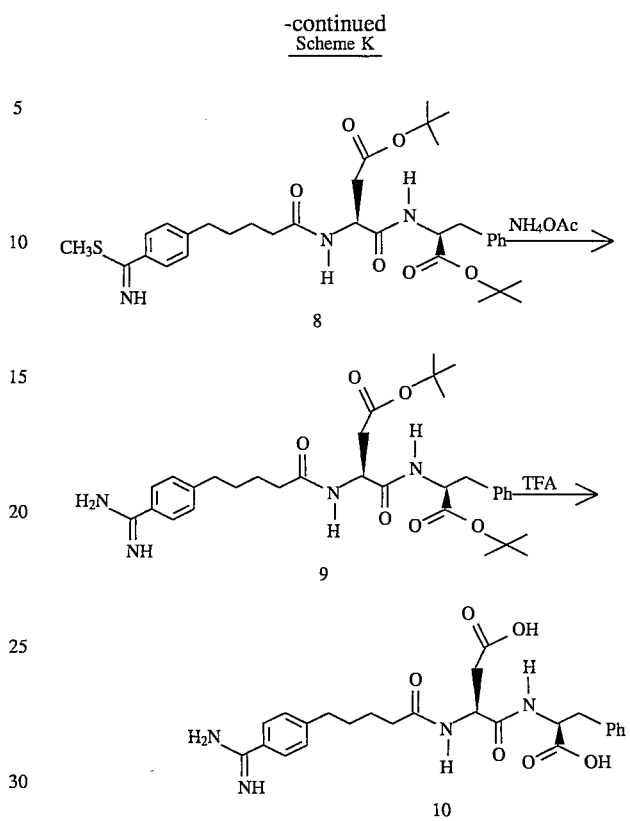

This invention also relates to a method of inhibiting platelet aggregation and more specifically, a method of treatment involving the administration of compounds of Formula I to achieve such inhibition.

For the inhibition of platelet aggregation compounds of Formula I may be administered orally, parenterally, or by inhalation spray or rectally in dosage unit formulations containing conventional nontoxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 10500 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples temperature is in degrees Celsius unless otherwise expressly set forth.

EXAMPLE 1

A. Preparation of 5-(p-cyanophenyl)-4-pentenoic acid (compound 3 of scheme K)

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8g, 375 mmol) and 100 mL of degassed anhydrous dimethylformamide (degassed by bubbling argon through for 10 min, dried over molecular sieves). A solution of 4-pentenoic acid (6.27 g, 62.6 mmol) and degassed anhydrous DMF (35 mL) was then added to the rapidly stirring reaction mixture at 23° C. After 21 hours at 23° C., the reaction mixture was poured slowly into a sodium carbonate solution (3%, 400 mL) and extracted with ethyl acetate (500 mL). The aqueous layer was treated with decolorizing carbon and filtered. Then, the aqueous layer was acidified to a pH of 2 with 10% HCl which afforded the title compound as a white solid (6.82 g, 54%): m.p. 150°–167° C. The above procedure affords the title compound in sufficient purity to take on to the next step without complications. An analytical sample was obtained by submitting the sample to further purification by flash chromatography (ethyl acetate:methylene chloride:acetic acid, 1:4:0.05) and recrystallization from ethyl acetate (2 times). The resulting product had the following properties: m.p. 154°–156° C.

Anal. Calcd. for $C_{12}H_{11}NO_2$: C, 71.63; H,5.51; N, 6.96. Found: C, 71.50; H, 5.54; N, 6.80.

B. Preparation of 5-(p-cyanophenyl)pentanoic acid (Compound 4 of scheme K)

A solution of 1.47 g (7.32 mmol) of the product of Section A in 90 mL of methanol was hydrogenated over 200 mg of 5% Pd / $CaCO_3$ at 5 psi hydrogen over a 1.2 h period. After removing the catalyst by filtration and evaporation of the solvent in vacuo, the residue was triturated with ether followed by hexane which afforded the title compound as a white solid. The resulting product had the following properties: m.p. 101°–102° C. Anal. Calcd. for $C_{12}H_{13}NO_2$: C, 70.92; H, 6.45; N, 6.89. Found: C, 70.71; H, 6.56; N, 6.87.

C. Preparation of 5-(p-cyanophenyl)pentanoyl-(S)-Aspartyl (O-t-butyl)-(S)-phenylalanine(O-t-butyl) (Compound 6 of Scheme K)

To a solution of 650 mg (3.20 mmol) of the product of Section B in 30 mL methylene chloride at 23° C. was added 727 mg (3.52 mmol) of N, N-dicyclohexylcarbodiimide, followed immediately by 1.26 g (3.20 mmol) of Asp(O-t-butyl)-Phe(O-t-but). The mixture was stirred for 20 h under an argon atmosphere. After dilution with ether (100 mL), the solids were removed by filtration, and the filtrate was concentrated in vacuo. The residue was dissolved in ethyl acetate (300 mL), washed with $KHSO_4$ (1N,1×80 mL), saturated $KHCO_3$ (1×80 mL), brine (1×80 mL), and dried ($Na_2SO_4$). Purification by flash chromatography (gradient 1 liter ethyl acetate:hexane 3:7 followed by 1.5 liters of ethyl acetate:hexane 1:1) afforded 1.48 g (80%) of the title compound as an oil.

D. Preparation of N-[N-[5-[4-aminoiminomethyl)phenyl-1-oxopentyl]-L-α-aspartyl] -L-phenylalanine, acetate salt (Compound 10 of Scheme K)

Hydrogen sulfide was bubbled through a solution of 740 mg (1.28 mmol) of the product of Section C in pyridine: triethylamine (12 mL: 1.2 mL) for 3 min at 23° C. After 24 h at 23° C. in an enclosed flask, the reaction mixture was concentrated under a steady stream of nitrogen. The residue was diluted with ethyl acetate (200 mL), washed with $KHSO_4$ (2N, 2×50 mL), brine (1×50 mL), and dried ($Na_2SO_4$). Concentration in vacuo afforded a quantitative yield of thioamide (Compound 7 of Scheme K).

Thioamide (Compound 7 of Scheme K) (690 mg, 1.13 mmol) was dissolved in a solution of acetone:iodomethane (14 mL: 1 mL). The reaction mixture was warmed to achieve reflux for 25 min. Concentration in vacuo afforded a quantitative yield of Compound 8 of Scheme K as the HI salt.

A solution of Compound 8 of Scheme K (705 mg, 1.13 mmol) and ammonium acetate (130 mg, 1.69 mmol) in methanol (10 mL) was warmed to achieve reflux for 3.5 h. After cooling to 23° C., the reaction mixture was concentrated under a steady stream of nitrogen in the hood which afforded a quantitative yield of Compound 9 of Scheme K.

A mixture of Compound 9 of Scheme K (390 mg, 0.656 mmol), trifluoroacetic acid (9 mL), and water (1 mL) was stirred at 23° C. for 1 h, and then evaporated under a slow nitrogen stream overnight. The product was purified on a reverse-phase C-18 functionalized silica gel column (1.9 cm×15 cm) using a linear gradient of 10% methanol/water 0.5% acetic acid to 100% methanol (40 min) with a flow rate of 3 mL/min to afford the title compound (Compound 10 of Scheme K). The product was verified by H NMR, C NMR, and fast atom bombardment mass spectrometry (MH$^+$=483).

The resulting product had the following properties: Anal. Calcd. for $C_{25}H_{30}N_4O_6$ plus 1.0 $H_2O$ and 0.8 acetic acid: C, 58.24; H, 6.47; N, 10.21. Found: C, 58.37; H, 6.17; N, 10.36.

EXAMPLE 2

Preparation of
N-[5-[4-(aminoiminomethyl)phenyl]-1-oxopentyl]-
N-L-α-aspartyl-L-phenylalanine, dimethyl ester

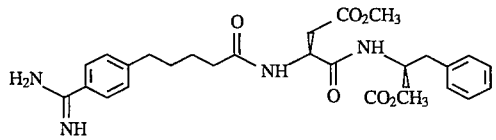

The Compound of Example 1, Section D was esterified in neat methanol containing a trace of sulfuric acid to afford the title compound which was purified in the manner of Example 1, Section D. The product was verified by C NMR ($CD_3CO_2D$) delta 24.4, 29.5, 34.5, 34.6, 35.2, 36.5, 49.0, 51.2, 51.5, 53.4, 124.8, 126.3, 127.3 127.9, 128.6, 128.7, 135.5, 149.2, 166.5, 170.9, 171.2, 174.5, 176.6; fast atom bombardment mass spectrometry (MH$^+$=511).

EXAMPLE 3

Preparation of
N-[6-[4-(aminoiminomethyl)phenyl]-1-oxohexyl]-
N-L-α-aspartyl-L-phenylalanine

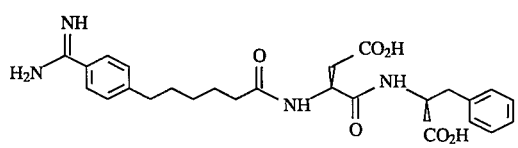

The title Compound was prepared in the manner of Example 1 with the following modifications: the 6-(p-cyanophenyl)- 5-hexenoic acid was prepared using standard Wittig chemistry from commercially available starting materials using the following procedure: Potassium bis(trimethylsilyl)amide (231 mL of a 0.66M solution in toluene, 152.5 mmol) was added dropwise to a suspension of 4-(carboxybutyl)triphenylphosphonium bromide in 500 mL of dry THF at 23° C. under a nitrogen atmosphere. After 1 h at 23° C., the reaction was cooled to −70° C., and 4-cyanobenzaldehyde (10.0 g, 76.3 mmol) in 50 mL of dry THF was added over 20 min. The reaction was allowed to warm to 23° C. and stir for 20 h. After concentration of the reaction mixture, the residue was dissolved in ether (500 mL), washed with water (300 mL) and aqueous sodium carbonate (300 mL, 5 %). The combined aqueous layers were acidified to a pH of 1, extracted with ether (2×300 mL), and dried ($Na_2SO_4$). After concentration in vacuo, the crude product was esterified by treatment with iodomethane (2 equiv.) in dimethylformamide Using potassium carbonate (2.5 equiv) as base. After concentration, the residue was dissolved in ethyl acetate (300 mL), washed with water (2×100 mL), brine (100 mL), and dried ($Na_2SO_4$). After concentration, the residue was purified by flash chromatography (ethyl acetate-:hexane, 1:1). A small portion (2.2 mmol) of the purified material was reduced using the conditions of Example 1 (section B) which afforded methyl 6-(p-cyanophenyl)-hexanoate. The methyl ester (2.6 mmol) was cleaved using aqueous sodium hydroxide (1N, 1.1 equiv) in methanol at 23° C. for 26 h. After concentration, the residue was dissolved in water (50 mL), acidified with HCL (1N) to a pH of 2, extracted with ether (2×200 mL), washed with water (1×100 mL), washed with brine (1×100 mL), and dried ($Na_2SO_4$). Concentration in vacuo afforded 6-(p-cyanophenyl)-hexanoic acid as a white solid: mp 61°–62° C. This starting material was used in place of the product of Section B, Example 1 in the procedure of Section C Example 1 to afford the title compound after completion of the sequence of reactions in the manner of Example 1 with the above substitution. The final product was verified by C NMR($CD_3CO_2D$) delta 26.2, 29.1, 29.2, 31.3, 36.1, 36.3, 36.4, 49.2, 49.3, 126.2, 127.7, 128.9, 129.4, 130.1, 130.4, 138.5, 151.0, 167.3 , 176.7 , 177.1, 178, 178.

Anal. Calcd. for $C_{26}H_{32}N_4O_6$ 0.3 $H_2O$: C, 62.21; H, 6.55; N, 11.16. Pound: C, 62.27; H, 6.48; N, 11.03.

EXAMPLE 4

Preparation of 3
S-[[5-[4-(aminoiminomethyl)phenyl]-1-oxopentyl]amino]-
4-oxo-4-[(2-phenylethyl)amino]butanoic acid

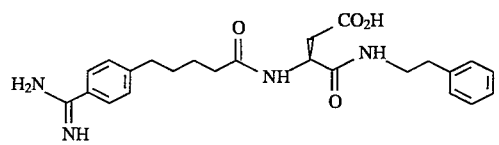

The title compound was prepared in the manner of Example 1 substituting Asp(O-t-but)-2-phenethyl amide for Compound 5 of Scheme K in Section C of Example 1. The product was verified by C NMR ($CD_3CO_2D$) delta 24.9, 30.0, 34.9, 35.0, 35.9, 40.9, 49.8, 125.2, 126.3, 127.9, 128.4, 128.6, 129.3, 138.7, 149.7, 166.3, 171.7, 174.9, 175.4; fast atom bombardment mass spectrometry (MH$^+$=439).

EXAMPLE 5

Preparation of
N-[N-[5-[3-(aminoiminomethyl)phenyl-1-oxopentyl]-
L-α-aspartyl]-L-phenylalanine

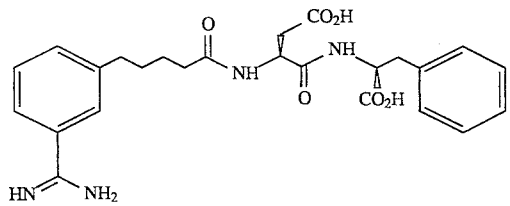

The title compound was prepared in the manner of Example 1 with the following changes in Section A of Example 1: 3-bromobenzonitrile was substituted for 4-bromobenzonitrile and the reaction was conducted at 50° C. The final product was verified by C NMR (CD$_3$CO$_2$D) delta 24.8, 29.9, 34.7, 35.1, 35.6, 36.8, 49.5, 53.8, 125.2, 126.8, 127.6, 128.4, 129.2, 134.3, 136.2, 143.9, 166.7, 171.6, 174.6, 174.8, 175.4; fast atom bombardment mass spectrometry (MH$^+$=483).

EXAMPLE 6

Preparation of 3S
[[5-[4-(aminoiminomethyl)phenyl]-1-oxopentyl]amino]-
4-[[2-4-(methoxyphenyl)ethyl]amino]-4-oxobutanoic
acid

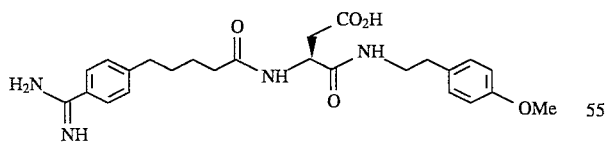

The title compound was prepared in the manner of Example 1 substituting Asp (O-t-butyl)-2-(p-methoxyphenyl)ethyl amide for Compound 5 of Scheme K in Section C of Example 1. The product was verified by C NMR (CD$_3$CO$_2$D) delta 25.6, 30.7, 34.6, 35.7, 35.8, 36.3, 41.7, 50.24, 53.7, 55.1, 114.5, 127.2, 128.5, 129.9, 130.2, 131.4, 132.2, 150.4, 167.2, 172.5, 176.4, 176.6; fast atom bombardment mass spectrometry (MH$^+$=469).

EXAMPLE 7

Preparation of
3S-[[5-[4-(aminoiminomethyl)phenyl]-1-
oxopentyl]amino]-
4-[(2-methylpropyl)amino]-4-oxobutanoic acid

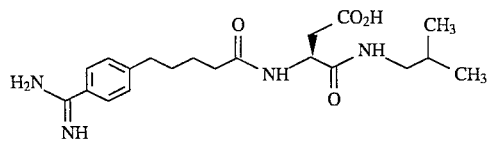

The title compound was prepared in the manner of Example 1 substituting Asp(O-t-butyl)-isobutyl amide for Compound 5 of Scheme K in Section C of Example 1. The product was verified by C NMR (CD$_3$CO$_2$D) delta 19.9, 25.6, 28.8, 30.7, 35.8, 35.9, 36.6, 47.6, 50.6, 125.9, 128.6, 130.0, 150.5, 167.5, 172.5, 175.5, 176.1; fast atom bombardment mass spectrometry (MH$^+$=391).

EXAMPLE 8

Preparation of
3S-[[5-[4-(aminoiminomethyl)phenyl]-1-
oxopentyl]amino]-
4-[[2-(1H-indol-3-yl)ethyl]amino]-4-oxobutanoic
acid

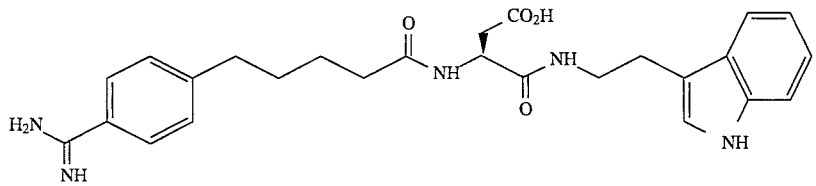

The title compound was prepared in the manner of Example 1 substituting Asp(O-t-butyl)-2-(3-indolyl)ethyl amide for Compound 5 of Scheme K in section c of Example 1. The product purity was verified by C NMR(CD$_3$CO$_2$D) delta 24.5, 24.9, 29.9, 35.0, 35.1, 35.6, 40.2, 49.7, 111.2, 111.7, 118.2, 118.8, 121.5, 122.4, 125.1, 127.3, 127.8, 129.2, 136.6, 149.7, 166.3, 171.5, 174.9, 175.4; fast atom bombardment mass spectrometry (MH$^+$=478).

EXAMPLE 9

Preparation of
N-[5-[4-(aminoiminomethyl)phenyl]-1-oxopentyl]-
N-L-α-aspartyl-L-valine

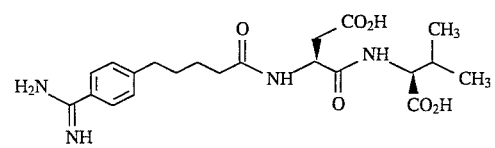

The title compound was prepared in the manner of Example 1 substituting Asp(O-t-butyl)-Val(O-t-butyl) for Compound 5 of Scheme K in Section C of Example 1. The product was verified by C NMR (CD$_3$CO$_2$D) delta 16.6, 18.0, 24.8, 29.8, 30.2, 34.8, 34.9, 35.4, 49.4, 57.5, 125.0, 127.7, 129.1, 149.5, 167.1, 172.1, 174.9, 175.0, 175.5; fast atom bombardment mass spectrometry (MH$^+$=435).

EXAMPLE 10

Preparation of
N-[5-[4-(aminoiminomethyl)phenyl]-1-oxo-4-pentynyl]-N-L-α-aspartyl-L-phenylalanine

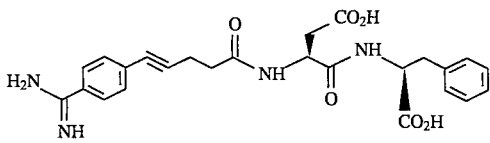

The title compound was prepared in the manner of Example 1 with the following modification: the 5-(p-cyanophenyl)-4-pentynoic acid was prepared using the following procedure. A solution of 4-pentynoic acid (2.15 g, 22 mmol), 4-bromobenzonitrile (3.64 g, 20 mmol), and piperidine (40 mL) was degassed by bubbling nitrogen through the solution for 5 min prior to the addition of tetrakis(triphenylphosphine)palladium (O) (240 mg, 0.2 mmol). The reaction vial was sealed and warmed to 80° C. for 1.5 h. After cooling to 23° C., the reaction mixture was diluted with ethyl acetate (200 mL), filtered, and concentrated in vacuo. The residue was diluted with ethyl acetate (300 mL), washed with 5% HCl (2×100 mL), washed with water (1×100 mL), and extracted with 3% sodium carbonate (2×200 mL). The basic aqueous layer was treated with decolorizing carbon, filtered, and acidified to pH=2. The resultant solid was filtered, washed with water, dried, and purified by flash chromatography (gradient ethyl acetate:methylene chloride:acetic acid 1:9:0.005) and fractional recrystallization (methylene chloride-ether) to afford 5-(p-cyanophenyl)-4-pentynoic acid as a white solid: m.p. 149°–152° C. The title compound was prepared in the manner of Example 1 with the following modification: The 5-(p-cyanophenyl)-4-pentynoic acid was substituted for Compound 4 of Scheme K. The product was verified by C NMR (DMSO-D6) delta 16.5, 34.8, 37.9, 52.1, 56.5, 80.5, 94.5, 126.8, 128.6, 128.7, 128.8, 128.9, 130.3, 132.4, 139.0, 166.2, 171.0, 171.1, 174.1, 176.2.

Anal Calcd. for $C_{25}H_{26}N_4O_6 \cdot 0.5\ H_2O$: C, 61.59; H, 5.58; N, 11.49. Found: C, 61.63; H, 5.73; N, 11.50.

EXAMPLE 11

Preparation of
N-[5-[4-(aminoiminomethyl)phenyl]-1-oxo-4E-pentenyl]-N-L-α-aspartyl-L-phenylalanine

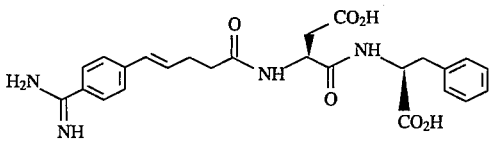

The title Compound was prepared in the manner of Example 1 with the following modification: The recrystallized Compound 3 of Scheme K was used and Section B of Example 1 was omitted. The product was verified by C NMR ($CD_3CO_2D$) delta 27.9, 33.8, 35.0, 36.0, 48.7, 53.2, 124.8, 125.7, 125.8, 127.2, 127.4, 128.3, 128.4, 132.0, 135.4, 142.5, 165.5, 170.6, 173.6, 173.9, 174.1: Crystals which formed during the concentration of the chromatography fractions containing product were collected, washed with water and dried (80° C., 0.1 mm) M.P. 215°–218° C. Anal. Calcd. for $C_{25}H_{28}N_4O_6$: C, 62.49; H, 5.87; N, 11.66. Found: C, 62.71; H, 6.07; N, 11.55.

EXAMPLE 12

Preparation of
N-[N-[5-[4-(aminoiminomethyl)phenyl]-1-oxopentyl]-L-α-aspartyl]-L-phenylalanine, diethyl ester

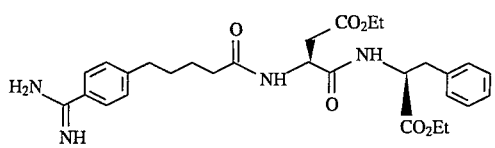

The final compound of Example 1, Section D was esterified by treatment with neat ethanol saturated with HCl gas for 20 h. After concentration in vacuo, the title compound was obtained through purification in the manner of Example 1, Section D. The product was verified by C NMR ($CD_3OD$) delta 13.6, 16.9, 25.2, 29.5, 34.8, 35.1, 35.4, 37.1, 50.3, 53.7, 61.0, 61.3, 123.9, 126.7, 127.8, 128.1, 128.9, 129.0, 135.5, 149.1, 165.6, 169.6, 170.5, 170.6, 176.1.

EXAMPLE 13

Preparation of
N-[N-[4-[4-(aminoiminomethyl)phenyl]-1-oxobutyl]-L-α-aspartyl]-L-phenylalanine

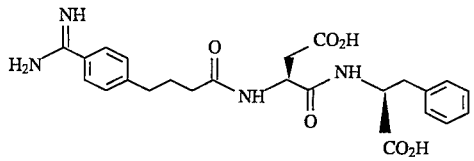

A. Preparation of 4-(P-Cyanophenyl)butanoic acid

The compound of A. was prepared in the manner of Example 1 with the following modifications:

4-(P-cyanophenyl)butanoic acid was substituted for 5-(-p-cyanophenyl)pentanoic acid.

The 4-(p-cyanophenyl)butanoic acid was prepared in the following manner: A mixture of 3-buten-1-ol (3.03 g, 42.0 mmol), 4-bromobenzonitrile (7.27 g, 39.9 mmol), triethylamine (6.05 g, 59.9 mmol), tri-o-tolylphosphine (0.841 g, 2.77 mmol), palladium acetate (0.224 g, 1 mmol), and acetonitrile (40 mL) was heated in a teflon sealed vial at 80° C. for 20 h. After cooling to 23° C., the reaction mixture was concentrated in vacuo, diluted with $Na_2CO_3$ (5%, 300 mL), extracted with ethyl acetate (2×300 mL), washed with brine (1× 100 mL), and dried ($Na_2SO_4$). After concentration in vacuo, purification of the resultant residue by flash chromatography (ethyl acetate:hexane, 1:1 afforded 4.06 g (58.7%) of 4-(p-cyanophenyl)-3-buten-1-ol. The product was converted to 4-(p-cyanophenyl)butan-1-ol by reduction of the double bond using the conditions of Example 1B. The 4-(p-cyanophenyl)butan-1-ol (1.49 g, 8.51 mmol) was oxidized to 4-(p-cyanophenyl)-butanoic acid by treatment with 8N Jones reagent (4 mL) in acetone (30 mL) at 10° C. for 10 min. The reaction was quenched with isopropanol (5 mL), concentrated in vacuo, diluted with H₂O (80 mL), extracted with ethyl acetate (2×200 mL), and washed with KHCO₃ (2× 250 mL). The aqueous layer was acidified with HCl (1N), extracted with ether (2×400 mL), and dried (Na₂SO₄). Concentration in vacuo afforded 1.07 g (78%, based on starting material consumed) of 4-(p-cyanophenyl)butanoic acid.

B. Preparation of N-[N-[4-[4-(aminoiminomethyl) phenyl]-1-oxobutyl]-L-α-aspartyl]-L-phenylalanine To a solution of 4-(p-cyanophenyl)butanoic acid (1.07 g, 5.27 mmol), dimethylformamide (10 mL), and pyridine (2 mL) was added N,N'-disuccinimidyl carbonate (1.35 g, 5.26 mmol) and 4-dimethylaminopyridine (64.4 mg, 0.527 mmol) under an argon atmosphere at 23° C. After 4 h, Asp (O-t-butyl)-Ph(O-t-butyl) (2.06 g, 5.27 mmol) was added followed immediately by N,N'-diisopropylethylamine (0.680 g, 5.26 mmol). After 20 h at 23° C., the reaction mixture was concentrated in vacuo. The residue was dissolved in ethyl acetate (250 mL), washed with KHSO₄ (1N, 100 mL), washed with brine (1×100 mL), and dried (Na₂SO₄). After concentration in vacuo, the residue was purified by flash chromatography (ethyl acetate:hexane, 2:3) to afford 1.70 g (56%) of the coupled product. The title compound was prepared by conversion of the benzonitrile to the benzamidine following the conditions of Example 1D followed by deprotection as in Example 1D. The final product was verified by C NMR (CD₃OD) delta 26.8, 34.7, 34.8, 35.4, 37.0, 50.0, 53.8, 125.8, 126.6, 127.8, 128.2, 129.2, 129.4, 136.8, 149.2, 166.6, 171.5, 172.6, 173.0, 174.3.

EXAMPLE 14

Preparation of
3S-[[5-[4-(aminoiminomethyl)phenyl]-
1-oxopentyl]amino]-4-[(2-carboxyethyl)
(2-methylpropyl)amino]-4-oxobutanoic acid

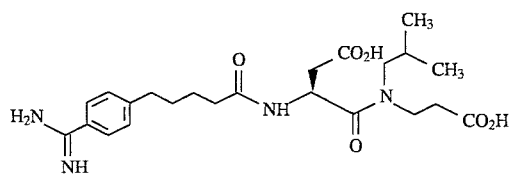

A. Preparation of
3S-[[5-[4-Cyanophenyl]-1-oxopentyl]-L-aspartic
acid-β-t-butyl ester To a solution of 5-(p-cyanophenyl)pentanoic acid (2.50 g, 12.3 mmol), dimethylformamide (10 mL), and pyridine (2 mL) was added N,N'-disuccinimidyl carbonate (3.15 g, 12.3 mmol) and 4-dimethylaminopyridine (34 mg, 0.278 mmol) under an argon atmosphere at 23° C. After 4 h, L-aspartic acid-β-t-butyl ester (2.33 g, 12.3 mmol) was added followed immediately by N,N'-diisopropylethylamine (2.15 mL, 12.3 mmol). After 20 h at 23° C., the reaction mixture was concentrated in vacuo. The residue was dissolved in ethyl acetate (250 mL), washed with KHSO₄ (1N, 100 mL), washed with brine (1×100 mL), and dried (Na₂SO₄). After concentration in vacuo, trituration with ethyl acetate:hexane (1:1) afforded 4.3 g (93%) of the title compound.

B. Preparation of
3S-[[5-[4-aminoiminomethyl)phenyl]-
1-oxopentyl]amino]-4-[(2-carboxyethyl)
(2-methylpropyl)amino] -4-oxabutanoic acid.

To a solution of 3S-[[5-[4-cyanophenyl]-1-oxopentyl] -L-aspartic acid-β-t-butyl ester (1.01 g, 2.70 mmol), dimethylformamide (10 mL), and pyridine (2 mL) was added N,N'-disuccinimidyl carbonate (0.685 g, 2.67 mmol) and 4-dimethylaminopyridine (0.030 g, 0.245 mmol) under an argon atmosphere at 23° C. After 4 h, N-[2-carbo-t-butoxyethyl]N'-(2-methylpropyl)amine (0.545 g, 2.71 mmol) was added followed immediately by N,N'-diisopropylethylamine (0.480 mL, 2.7 mmol). After 20 h. at 23° C., the reaction mixture was concentrated in vacuo. The residue was dissolved in ethyl acetate (250 mL), washed with KHSO₄ (1N, 100 mL), washed with brine (1×100 mL), and dried (Na₂SO₄). After concentration in vacuo, purification by flash chromatography (ethyl acetate:hexane 1:1) afforded the coupled product (1.00 g, 67%). The title compound was prepared by conversion of the benzonitrile to the benzamidine following the conditions of Example 1D followed by deprotection as in Example 1D. The final product was verified by C NMR (CD₃OD) delta 19.3, 19.4, 25.3, 26.8, 28.1, 30.4, 31.7, 3.2, 35.3, 36.6, 36.7, 43.5, 44.0, 46.4, 46.5, 53.1, 55.7, 126.1, 128.0, 129.4, 149.8, 167.1, 171.0, 171.1, 172.9, 173.8, 174.3, 174.5.

Anal. Calcd. for C₂₃H₃₄N₄O₆ plus 1.5 CF₃CO₂H: C, 49.33; H, 5.57; N, 8.85. Found: C, 49.32; H, 5.64; N, 8.83.

EXAMPLE 15

Preparation of
3S-[[5-[4-(aminoiminomethyl)phenyl]-1-
oxopentyl]amino]-
4-[(2-carboxyethyl)(phenylmethyl)
amino]-4-oxobutanoic acid

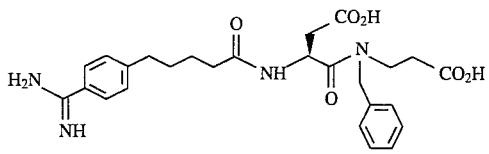

The title compound was prepared in the manner of Example 14 substituting N-[2-carbo-t-butoxyethyl]-N'-benzylamine for N-[2-carbo-t-butoxyethyl]N'-(2-methylpropyl)amine in procedure 14B. The product was verified by C NMR (CD₃CO₂D) (amide rotamers) delta 24.9, 29.8, 31.3, 32.4, 34.8, 36.3, 42.8, 43.1, 46.1, 46.3, 48.7, 52.1, 125.1, 127.1, 127.3, 127.8, 128.6, 128.7, 129.1, 136.8, 137.0, 149.1, 166.7, 172.5, 174.9; Fast Atom Bombardment Mass Spectrometry (MH⁺)=497.

Anal. Calcd. for C₂₆H₃₂N₄O₆ plus 1CF₃CO₂H and 1.0 H₂O: C, 53.50; H, 5.61; N, 8.91. Found: C, 53.46; H, 6.07; N, 8.76.

EXAMPLE 16

Preparation of
3S-[[5-[4-(aminoiminomethyl)phenyl]-1-oxopentyl)amino]-
4-[(2-carboxyethyl)(2-(4-methoxyphenyl)ethyl]amino]-
4-oxobutanoic acid

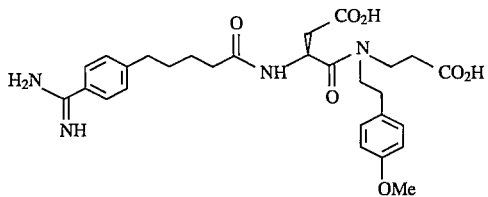

The title compound was prepared in the manner of Example 14 substituting N-[2-carbo-t-butoxyethyl]N'-[2-(4-methoxyphenyl)ethyl]amine for N-[2-carbo-t-butoxyethyl] N'-(2-methylpropyl)amine in procedure 14B. The product was verified by C NMR (CD$_3$OD) (amide rotamers) delta 25.4, 30.5, 32.2, 32.7, 33.5, 34.5, 35.4, 36.5, 43.4, 44.3, 46.4, 50.8, 54.8, 114.1, 114.3, 125.5, 128.1, 129.6, 130.0, 130.2, 130.6, 149.9, 158.8, 166.8, 1.71.8, 172.9, 173.6, 174.4, 174.5

Anal. Calcd. for $C_{28}H_{36}N_4O_7$ plus 1.0 $CF_3CO_2H$ and 0.5 $H_2O$: C, 54.29; H, 5.77; N, 8.44. Found: C, 54.26; H, 5.78; N, 8.24.

EXAMPLE 17

Preparation of
3S-[[5-[4-(Aminoiminomethyl)phenyl]-1-oxopentyl]amino]-
4-[(2-carboxyethyl)(2-phenylethyl)amino]-4-oxobutanoic acid

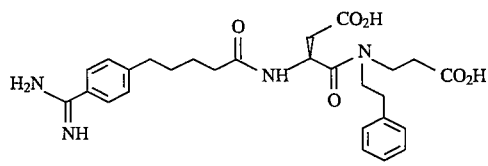

The title compound was prepared in the manner of Example 14 substituting N-[2-carbo-t-butoxyethyl]N'-2-(phenyl)ethylamine for N-[2-carbo-t-butoxyethyl]-N'-(2-methylpropyl)amine in procedure 14B. The product was verified by C NMR (CD$_3$CO$_2$D) (amide rotamers) delta 22.3, 27.2, 28.7, 29.3, 30.5, 33.7, 34.1, 34.5, 40.6, 41.5, 43.4, 45.8, 46.1, 48.4, 122.8, 123.9, 124.1, 125.3, 125.8, 126.0, 126.1, 126.3, 135.6, 136.4, 147.3, 164.6, 169.5, 172.3, 172.6, 174.2.

Anal. Calcd. for $C_{27}H_{34}N_4O_6$ plus 1.0 $CF_3CO_2H$ and 1.0 $H_2O$: C, 54.20; H, 5.80; N, 8.72. Found: C, 53.89; H, 5.85; N, 8.94.

EXAMPLE 18

Preparation of
N-[N-[5-[4-(aminoiminomethyl)phenyl]-1-oxopentyl]-
L-α-aspartyl] -N-methyl-L-phenylalanine

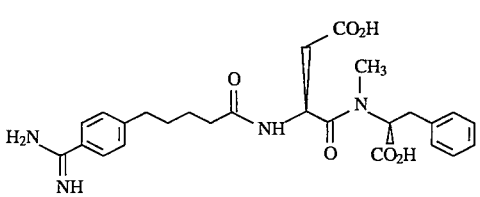

The title compound was prepared in the manner of Example 14 substituting N-methyl-L-phenylalanine for N-[2-carbo-t-butoxyethyl]-N'-(2-methylpropyl)amine in the procedure 14B. The product was verified by C NMR (CD$_3$OD) (amide rotamers) delta 24.8, 24.9, 29.9, 30.0, 32.8, 33.0, 34.0, 34.1, 34.9, 35.5, 35.7, 35.8, 45.6, 46.0, 46.2, 59.9, 63.4, 125.5, 126.2, 126.3, 126.4, 126.6, 127.6, 128.1, 128.6, 128.7, 129.1, 137.2, 137.5, 149.5, 166.9, 171.6, 171.7, 172.3, 173.5, 174.0.

Anal. Calcd. for $C_{26}H_{32}N_4O_6$ plus 1.0 $CF_3CO_2H$ and 1.0 $H_2O$: C, 53.50; H, 5.61; N, 8.91. Found: C, 53.75; H, 5.45; N, 8.89.

EXAMPLE 19

Preparation of
R-[[[[2S-[4-(aminoiminomethyl)phenyl]-1-oxopentyl]
amino]-3-carboxy-1-oxopropyl]amino]
benzenepentanoic acid

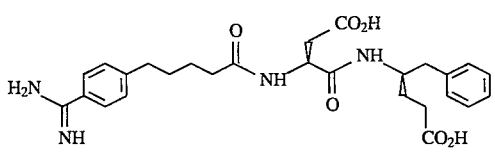

The title compound was prepared in the manner of Example 14 substituting R-4-amino-5-phenylpentanoic acid for N-[2-carbo-5-butoxyethyl]-N'-(2-methyl)propylamine in procedure 14B. The product was verified by C NMR (DMSO-D$_6$) delta 25.4, 29.7, 30.1, 30.8, 31.2, 35.5, 35.6, 37.1, 50.4, 126.4, 126.8, 128.9, 129.7, 130.0, 139.5, 149.7, 166.7, 171.1, 172.5, 172.8, 175.1.

Anal. calcd. for $C_{27}H_{34}N_4O_6$ plus 1.25 $CF_3CO_2H$ and 1.0 $H_2O$: C, 52.87; H, 5.45; N, 8.36. Found: C, 53.14; H, 5.71; N. 8.25.

EXAMPLE 20

Preparation of
N-[N-[5-[4-(aminoiminomethyl)phenyl]-
1,4-dioxopentyl]-L-α-aspartyl]-L-phenylalanine

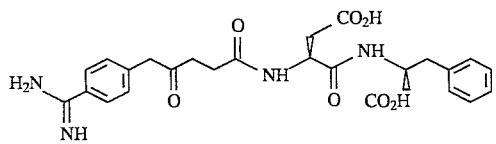

A. To a solution of tetrakis(triphenylphosphine) palladium (O) (100 mg, 0.09 mmol), triethylamine (1.45 g, 14.3 mmol), in 50 mL of acetonitrile was added 4-bromobenzonitrile (1.82 g, 10 mmol) and 4-pentynoic acid (1.0 g, 10.2 mmol). The reaction mixture was warmed to 82° C. for 4 h followed by cooling to 23° C. After concentration in vacuo, the reside was purified by flash chromatography (gradient—1 liter hexane:ethyl acetate (4:1) followed by hexane:ethyl acetate 1:1) which afforded the enol lactone (1.48 g, 74%).

Anal. Calcd. for $C_{12}H_9NO_2$: C, 72.35; H, 4.55; N, 7.03. Found: C, 72.18; H, 4.61; H, 7.04.

B. A mixture of the enol lactone (287 mg, 1.43 mmol), Asp(O-t-butyl)-Phe(O-t-butyl) (565 mg, 1.43 mmol) and acetonitrile (15 mL) was warmed to 82° C. for 40 h followed by cooling to 23° C. After concentration in vacuo, the residue was purified by flash chromatography (hexane:ethyl acetate 1:1) which afforded the amide (748 mg, 88.4%).

C. The title compound was prepared by conversion of the benzonitrile to the benzamidine following the conditions of Example 1D followed by deprotection as in Example 1D. The final product was verified by C NMR (DMSO-$d_6$) 28.9, 36.6, 37.1, 48.3, 49.8, 54.6, 125.8, 127.0, 127.6, 127.7, 129.4, 130.1, 138.1, 140.7, 165.9, 169.9, 171.0, 172.6, 174.1, 206.2.

Anal. Calcd. for $C_{25}H_{28}N_4O_7$ plus $H_2O$: C, 58.36; H, 5.88; N, 10.89. Found: C, 58.69; H, 5.90; N, 10.79.

EXAMPLE 21

Preparation of
N-[N-[5-[4-(aminoiminomethyl)phenyl]-
4-hydroxy-1-oxopentyl]-L-α-aspartyl]-L-phenylalanine

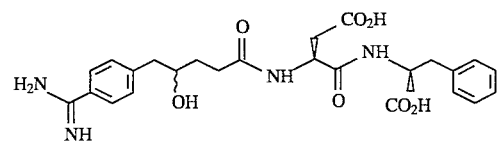

The ketone group of product (622 mg, 105 mmol) of Example 20 B was reduced to the alcohol by treatment with $NaBH_4$ (65.0 mg, 1.72 mmol) in isopropanol (5 mL) at 23° C. for 2 h. The reaction was quenched through the addition of 5% HCl (5 mL) and subsequent stirring for 1 h at 23° C. The reaction mixture was diluted with ethyl acetate (150 mL), washed with water (50 mL), brine (50 mL), and dried ($Na_2SO_4$). After concentration in vacuo, the residue was purified by flash chromatography (gradient ethyl acetate:hexane 3:2 to ethyl acetate 100% to afford the alcohol (152 mg).

The title compound was prepared by conversion of the benzonitrile to the benzamidine following the conditions of Example 1D followed by deprotection as in Example 1D. The final product was verified by C NMR (CD$_3$OD) delta 27.2, 29.3, 35.9, 37.9, 38.7, 42.9, 50.7, 54.1, 55.4, 82.2, 127.8, 127.9, 128.9, 129.4, 130.1, 130.2, 131.4, 138.7, 145.3, 168.4, 170.1, 173.2, 174.8, 179.6.

EXAMPLE 22

Preparation of
N-[N-[5-[4-(aminoiminomethyl)phenyl]-
1-oxo-4Z-pentenyl]-L-α-aspartyl]-L-phenylalanine

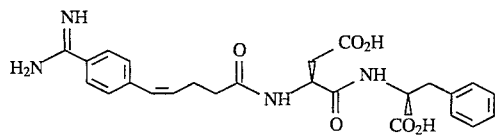

A solution of (267 mg, 0.46 mmol) N-[5-(p-cyanophenyl)-1-oxo-4-pentynyl]-N-L-α-aspartyl-L-phenylalanine of Example 10 in 50 mL of THF was hydrogenated over quinoline treated 5% Pd/CaCO$_3$ at 5 psi hydrogen over a 50 minute period. After removing the catalyst by filtration and evaporation of the solvent in vacuo, the residue was diluted with ether (200 mL), washed with KHSO$_4$ (1N, 2×50 mL), and dried (Na$_2$SO$_4$). After concentration in vacuo, the residue was purified by flash chromatography (hexane:ethyl acetate 7:3) to afford the cis alkene (232 mg, 87%).

The title compound was prepared by conversion of the benzonitrile to the benzamidine following the conditions of Example 1D followed by deprotection as in Example 1D. The final product was verified by C NMR (CD$_3$CO$_2$D) delta 27.1, 37.8, 38.4, 40.1, 52.8, 56.7, 128.3, 129.4, 130.4, 130.9, 131.0, 131.8, 132.0, 135.8, 139.2, 145.7, 168.9, 174.6, 176.9, 177.6.

Anal. Calcd. for $C_{25}H_{28}N_4O_6$ plus 0.5 $H_2O$ and 0.3 HOAC: C, 60.58; H, 6.00; N, 11.04. Found: C, 60.55; H, 5.91; N, 10.97.

EXAMPLE 23

Preparation of
N-[N-[6-[3-(aminoiminomethyl)phenyl]-
1-oxo-5Z-hexenyl]-L-α-aspartyl]-L-phenylalanine

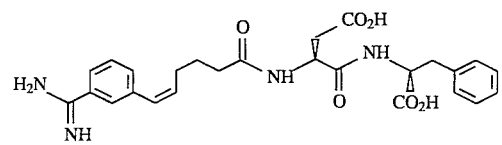

The title compound was prepared in the manner of Example 1 with the following modifications: the 6-(m-cyanophenyl)- 5-(Z)-hexenoic acid was prepared using standard Wittig chemistry following the procedure of Example 3 with the following substitutions sodium bis(trimethylsilyl)amide for potassium bis(trimethylsilyl)amide and 3-cyanobenzaldehyde for 4-cyanobenzaldehyde. The 6-(m-cyanophenyl)-5(Z)-hexenoic acid was obtained after purification by flash chromatography (hexane:ethyl acetate:acetic acid 8:2:0.005) and fractional crystallization (ether:hexane) [note: following this procedure one can separate the E and Z isomers on a preparative scale].

The reduction step of Example 1C was omitted. The final product was verified by C NMR (DMSO-$d_6$) delta 25.1, 27.6, 34.5, 37.0, 37.1, 49.9, 54.7, 125.8, 125.9, 127.4, 127.5, 127.7, 128.1, 128.7, 128.9, 129.2, 129.4, 133.2, 134.1, 137.7, 138.2, 166.1, 170.2, 171.9, 172.8, 174.6.

Anal. Calcd. for $C_{26}H_{30}N_4O_6$: C, 63.15; H, 6.11; N, 11.33. Found: C, 62.95; H, 6.11; N, 11.21.

EXAMPLE 24

Preparation of
N-[N-[6-[4-(aminoiminomethyl]phenyl]-1-oxohexyl]-L-α-aspartyl]-L-phenylalanine

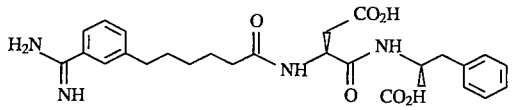

The title compound was prepared in the manner of Example 23 except that the reduction step of Example 1C was not omitted. The product was verified by C NMR ($CD_3CO_2D$) delta 26.2, 29.2, 31.6, 36.1, 36.5, 37.0, 38.1, 50.8, 55.3, 126.4, 127.9, 128.9, 129.1, 129.5, 130.5, 135.4, 137.5, 145.4, 167.8, 172.8, 176.0, 176.1, 176.7.

Anal. Calcd. for $C_{26}H_{32}N_4O_6$ plus 0.25 $H_2O$: C, 62.32; H, 6.54; N, 11.18. Found C, 62.32; H, 6.87; N, 11.13.

EXAMPLE 25

Preparation of
N-[N-[2-[[6-(aminoiminomethyl)-2-naphthalenyl]oxy]-1-oxoethyl]-L-α-aspartyl]-L-phenylalanine

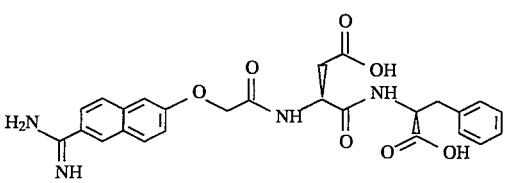

The title compound was prepared in the manner of Example 1 with the following modification: 2-[[6-(cyano)-2-naphthalenyl]oxy]acetic acid was substituted for 5-(p-cyanophenyl)pentanoic acid in Section C of Example 1.

Anal. Calcd. for $C_{26}H_{26}N_4O_7$ plus 0.25 $CF_3CO_2H$ and 0.5 $H_2O$: C, 58.51; H, 5.05; N, 10.30. Found: C, 58.52; H, 5.04; N, 10.15.

EXAMPLE 26

Preparation of
N-[N-[3-[6-(aminoiminomethyl)-2-naphthalenyl]-1-oxopropyl]-L-α-aspartyl]-L-phenylalanine

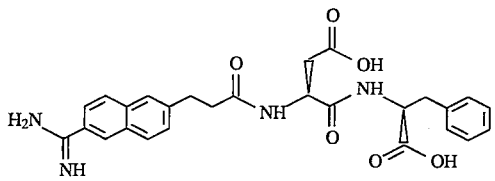

The title compound was prepared in the manner of Example 1 with the following modification: 3-[6-(cyano)-2-naphthalenyl] propionic acid was substituted for 5-(p-cyanophenyl)pentanoic acid in Section C of Example 1.

Anal. Calcd. for $C_{27}H_{28}N_4O_6$ plus 0.25 $H_2O$: C, 63.71; H, 5.64; N, 11.01. Found: C, 63.58; H, 5.74; N, 10.87.

EXAMPLE 27

The platelet receptor binding affinity and aggregation inhibitory potency of representative compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10⁸ platelets per ml. 400 for 5-(p-cyanophenyl)pentanoic acid in Section C of Example 1.

Anal. Calcd. for $C_{27}H_{28}N_4O_6$ plus 0.25 $H_2O$: C, 63.71; H, 5.64; N, 11.01. Found: C, 63.58; H, 5.74; N, 10.87.

EXAMPLE 28

The platelet receptor binding affinity and aggregation inhibitory potency of representative compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μl of the PRP preparation and 50 μl of the compound to be tested or saline were preincubated for 1 minute at 37° C. in a BioData aggregometer (BioData, Horsham, Pa.). 50 μl of adenosine 5'diphosphate (ADP) (50 μm final concentration) was added to the cuvettes and the aggregation was monitored for 1 minute. All compounds are tested in duplicate. Results are calculated as follows:

Percent of control=[(maximal OD minus initial OD of compound) divided by (maximal OD minus initial OD of control saline)]× 100. The % inhibition=100– (percent of control).

The compounds tested and their median inhibitory concentrations (IC$_{50}$) are recorded in Table A. IC$_{50}$'s (if a compound showed 50% inhibition) were calculated by linear regression of the dose response curve. The assay results for the representative compounds of the present invention are set forth in Table A.

Fibrinogen Binding Assay

Fibrinogen binding was performed essentially as described by Plow et al., *Blood* 70, 110–115 (1987). Briefly, blood from humans who had not been given any antiplatelet drugs in the previous two weeks was collected into 1/10th volume of CCD buffer (100 mM sodium citrates, 136 mM glucose, pH 6.5). The blood was centrifuged for 3 min at 1000×g and platelet rich plasma was transferred to a plastic tube with a plastic pipet and placed on ice. After 15 minutes, ½ volume of ice cold CCD buffer was added and the sample was centrifuged at 900×g for 10 min at 2° C. The supernatant was decanted and the platelet pellet was gently resuspended in ½ the original volume of ice cold modified Tyrode's buffer (137 mM NaCl, 2.6 mM KCl, 12 mM NaHCO$_3$, 5.5 mM glucose, 15 mM HEPES, 0.5% BSA, pH 7.4). After incubating for 30 minutes at 37° C., the platelet count was adjusted to 4×10$^8$ platelets/ml with modified Tyrode's buffer. To test samples (final concentration=1×10$^8$ platelets/ml) were added in sequence: ADP (10 μM), CaCl$_2$ (2 mM), test compound, and $^{125}$I-fibrinogen (0.3 μM) to the aforesaid final concentrations in a volume of 200 μl. The samples were incubated for 40 min at 37° C. and 50 μl aliquots were centrifuged at 8,000×g through a 20% sucrose solution (400 μl). The tubes were quick frozen and the tips containing the platelet pellet were cut and assayed for bound $^{125}$I-fibrinogen by gamma scintillation counting. Specific binding was determined in each test by subtracting from the total binding the amount of $^{125}$I-fibrinogen bound in the presence of a 60-fold excess of unlabeled fibrinogen. The potency of test compounds (IC$_{50}$) was determined as the concentration of compound required to inhibit 50% of 125I-fibrinogen binding.

INHIBITION OF EX VIVO COLLAGEN INDUCED AGGREGATION BY COMPOUNDS OF THE INVENTION

PURPOSE—The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in an aggregometer and used as Control. Compounds are administered, either intragasterically (either by capsule or stomach tube or intravenously. Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of 24 hours or until the platelet aggregation returns to control levels. (If aggregation is still inhibited after 7 hours, a blood sample is drawn the following morning and tested.) Duration of activity is determined by the length of time platelet aggregation is inhibited after compound administration. The assay results for representative compounds of the present invention in the aforementioned Assay are set forth in Table A.

N-[N-[5-[4-(aminoiminomethyl)phenyl]-1-oxopentyl]-L-α-aspartyl] -L-phenylalanine was tested in a canine intravenous infusion model and the ED$_{50}$ was 0.32 μg/kg/min.

In Table A the designation "NT" means "Not Tested".

TABLE A

| | IN-VITRO PLATELET AGGREGATION IN PRP | | | | EX-VIVO COLLAGEN INDUCED AGGREGATION | | |
| --- | --- | --- | --- | --- | --- | --- | --- |
| Compound | Dog Prp IC$_{50}$ Micro M | % Inhi- bition | Test Concen- tration | Human Fg binding IC$_{50}$ Micro M | Dose Tested mg/kg | Max % Inhi- bition | Route |
| N-[N-[6-[4-(aminoiminomethyl)phenyl]-i-oxohexyl]-L-α-aspartyl]-L-phenylalanine | 1.1 | 100 | 1 × 10$^{-5}$ | NT | NT | NT | NT |
| N-[N-[5-[4-(aminoiminomethyl)phenyl]-1-oxopentyl]-L-α-aspartyl]-L-phenylalanine, acetate | 0.053 | 100 | 1 × 10$^{-5}$ | 0.0083 | 0.006 0.003 | 84 31 | IV IV |
| 3S-[[(5-[4-(aminoiminomethyl)phenyl]-1-oxopentyl]amino]-4-oxo-4-[(2phenylethyl)amino]butanoic acid, acetate | 1.9 | 100 | 1 × 10$^{-5}$ | 0.2 | NT | NT | NT |
| N-[N-[5-[3-(aminoiminomethyl)phenyl]-1-oxopentyl]-L-α-aspartyl]-L-phenylalanine | | 25 | 1 × 10$^{-5}$ | NT | NT | NT | NT |
| 3S-[[5-[4-(aminoiminomethyl)phenyl]-1-oxopentyl]amino]-4-[[2-(4- | 0.42 | 100 | 1 × 10$^{-5}$ | NT | NT | NT | NT |

TABLE A-continued

| | IN-VITRO PLATELET AGGREGATION IN PRP | | | | EX-VIVO COLLAGEN INDUCED AGGREGATION | | |
|---|---|---|---|---|---|---|---|
| Compound | Dog Prp $IC_{50}$ Micro M | % Inhibition | Test Concentration | Human Fg binding $IC_{50}$ Micro M | Dose Tested mg/kg | Max % Inhibition | Route |
| methoxyphenyl)ethyl]amino]-4-oxobutanoic acid | | | | | | | |
| 3S-[[5-[4-(aminoiminomethyl)phenyl]-1-oxopentyl]amino]-4-[(2-methylpropyl)amino]-4-oxobutanoic acid | 0.70 | 100 | $1 \times 10^{-5}$ | NT | 0.1 | 100 | IV |
| 3S-[[(5-[4-(aminoiminomethyl)phenyl]-1-oxopentyl]amino]-4-[[2-(1H-indol-3-yl)ethyl]amino]-4-oxobutanoic acid | 0.28 | 100 | $1 \times 10^{-5}$ | NT | NT | NT | NT |
| N-[N-[5-[4-(aminoiminomethyl)phenyl]-1-oxopentyl]-L-α-aspartyl]-L-valine | 0.13 | 100 | $1 \times 10^{-5}$ | NT | NT | NT | NT |
| N-[N-[5-[4-(aminoiminomethyl)phenyl]-1-oxopentyl]-L-α-aspartyl]-L-phenylalanine, dimethyl ester | 0.40 | 100 | $1 \times 10^{-5}$ | NT | NT | NT | NT |
| N-[N-[5-[4-(aminoiminomethyl)phenyl]-1-oxo-4-pentynyl]-L-α-aspartyl]-L-phenylalanine | 0.09 | 100 | $1 \times 10^{-5}$ | 0.006 | 0.1 0.01 0.005 | 100 83 29 | IV IV IV |
| 3S-[[5-[4-(aminoiminomethyl)phenyl]-1-oxopentyl]amino]-4-[(2-carboxyethyl)(phenylmethyl)amino]-4-oxobutanoic acid | 4.3 | 100 | $1 \times 10^{-5}$ | NT | NT | NT | NT |
| N-[N-[5-[4-(aminoiminomethyl)phenyl]-1-oxo-4E-pentenyl]-L-α-aspartyl]-L-phenylalanine | 0.082 | 100 | $1 \times 10^{-5}$ | 0.007 | NT | NT | NT |
| N-[N-[2-[[3-[4-(aminoiminomethyl)phenyl]-1-oxopropyl]methylamino]-1-oxoethyl]-L-α-aspartyl]-L-phenylalanine | 0.7 | 100 | $1 \times 10^{-5}$ | NT | NT | NT | NT |
| 3S-[[5-[4-(aminoiminomethyl)phenyl]-1-oxopentyl]amino]-4-[(2-carboxyethyl)(2-phenylethyl)amino]-4-oxobutanoic acid | 10 | 53 | $1 \times 10^{-5}$ | NT | NT | NT | NT |
| 3S-[[5-[4-(aminoiminomethyl)phenyl]-1-oxopentyl]amino]-4-[(2-carboxyethyl)[2-(4-methoxyphenyl)ethyl]amino]-4-oxobutanoic acid | | 66 | $1 \times 10^{-5}$ | NT | NT | NT | NT |
| N-[N-[5-[4-(aminoiminomethyl)phenyl]-1-oxo-4Z-pentenyl]-L-α-aspartyl]-L-phenylalanine | 0.6 | 100 | $1 \times 10^{-5}$ | NT | NT | NT | NT |
| 3S-[[5-[4-(aminoiminomethyl)phenyl]-1-oxopentyl]amino]-4-[(2-carboxyethyl)(2-methylpropyl)amino]-4-oxobutanoic acid | | 14 | $1 \times 10^{-5}$ | NT | NT | NT | NT |
| N-[N-[5-[4-(aminoiminomethyl)phenyl]-1-oxopentyl-L-α-aspartyl]-N-methyl-L-phenylalanine | 1.5 | 100 | $1 \times 10^{-5}$ | NT | NT | NT | NT |
| R-[[[[2S-[4-(aminoiminomethyl)phenyl]-1-oxopentyl]amino]-3-carboxy-1-oxopropyl]amino]benzenepentanoic acid | 0.7 | 100 | $1 \times 10^{-5}$ | NT | NT | NT | NT |
| N-[N-[5-[4-(aminoiminomethyl)phenyl]-1,4-dioxopentyl]-L-α-aspartyl]-L-phenylalanine | 0.18 | 100 | $1 \times 10^{-5}$ | NT | NT | NT | NT |
| N-[N-[6-[4-(aminoiminomethyl)phenyl]-1-oxohexyl]-L-α-aspartyl]-L-phenylalanine | 5.8 | 77 | $1 \times 10^{-5}$ | NT | NT | NT | NT |
| N-[N-[5-[4-(aminoiminomethyl)phenyl]-4-hydroxy-1-oxopentyl]-L-α-aspartyl]-L-phenylalanine | | 15 | $1 \times 10^{-5}$ | NT | NT | NT | NT |
| N-[N-[6-[3-(aminoiminomethyl)phenyl]-1-oxo-5Z-hexenyl]-L-α-aspartyl]-L-phenylalanine | 4.3 | 100 | $1 \times 10^{-5}$ | 0.600 | NT | NT | NT |
| N-[N-[5-[4-(aminoiminomethyl)phenyl]-1-oxopentyl]-L-α-aspartyl]-L-phenylalanine, diethyl ester | NT | NT | NT | NT | .025 | 39 | IG |
| N-[N-[4-[4-(aminoiminomethyl)phenyl]-1-oxobutyl]-L-α-aspartyl]-L-phenylalanine | | 4 | $1 \times 10^{-5}$ | NT | NT | NT | NT |
| N-[N-[2-[[6-aminoiminomethyl)-2-naphthalenyl]oxy]-1-oxoethyl-L-α-aspartyl]-L-phenylalanine | 1.1 | 100 | $1 \times 10^{-5}$ | NT | NT | NT | NT |
| N-[N-[3-[6-(aminoiminomethyl)-2-naphthalenyl]-1-oxopropyl]-L-α-aspartyl]-L-phenylalanine | 5.5 | 100 | $1 \times 10^{-5}$ | NT | NT | NT | NT |

What we claim is:
1. A compound of the formula

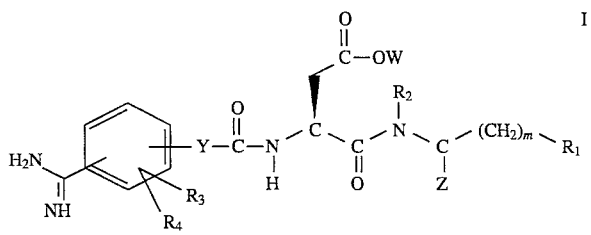

or a pharmaceutically acceptable salt thereof, wherein $R_1$ is selected from phenyl; substituted phenyl wherein each substituent can be selected from the group consisting of alkyl having 1 to 6 carbon atoms, halo, alkoxy having 1 to 6 carbon atoms, trifluoromethyl, hydroxy and carboxyl; alkyl having 1 to 6 carbon atoms wherein said alkyl may be substituted by alkyl having 1 to 4 carbon atoms; carboxyl; and a fully unsaturated heteromonocyclic ring structure having 5 or 6 ring carbon atoms wherein 1 of the ring carbon atoms is replaced by nitrogen, oxygen or sulfur and wherein said heteromonocyclic ring is fused to a benzene ring;

$R_2$ is hydrido; alkyl having 1 to 6 carbon atoms; phenyl; phenylalkyl wherein the alkyl is 1 to 6 carbon atoms and wherein the phenyl ring may be independently substituted one or more times by a substituent selected from alkyl having 1 to 6 carbon atoms, halo, and alkoxy having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms; alkynyl having 2 to 6 carbon atoms;

Z is hydrido, carboxyl, alkoxycarbonyl having 1 to 6 carbon atoms or alkylcarboxyl having 1 to 6 carbon atoms; and m is an integer from 0 to 4.

2. A compound according to claim 1 of the formula

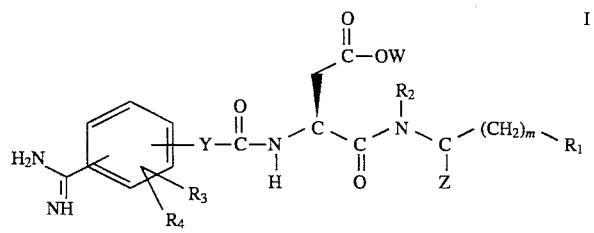

or a pharmaceutically acceptable salt thereof, wherein $R_1$ is selected from phenyl or substituted phenyl wherein each substituent can be selected from the group consisting of alkyl having 1 to 6 carbon atoms, halo, alkoxy having 1 to 6 carbon atoms, trifluoromethyl, hydroxy and carboxyl;

$R_2$ is hydrido or alkyl having 1 to 6 carbon atoms;

$R_3$ and $R_4$ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

3. A compound according to claim 2 which is N-[N-[5-[4-(aminoiminomethyl)phenyl-1-oxopentyl]-L-α-aspartyl]-L-phenylalanine, dimethyl ester.

4. A compound according to claim 2 which is N-[N-[5-[4-(aminoiminomethyl]phenyl]-1-oxopentyl]-L-α-aspartyl]-L-phenylalanine, diethyl ester.

5. A compound according to claim 2 wherein Z is carboxyl.

6. A compound according to claim 5 which is N-[N-[5-[4-(aminoiminomethyl)phenyl]-1-oxopentyl]-L-α-aspartyl]-L-phenylalanine.

7. A compound according to claim 5 which is N-[N-[5-[4-(aminoiminomethyl)phenyl]-1-oxopentyl]-L-α-aspartyl]-L-phenylalanine acetate.

8. A compound according to claim 5 which is N-[N-[5-[3-(aminoiminomethyl)phenyl]-1-oxopentyl]-L-α-aspartyl]-L-phenylalanine.

9. A compound according to claim 5 which is N-[N-[5-[4-(aminoiminomethyl)phenyl]-1-oxo-4-pentynyl]-L-α-aspartyl]-L-phenylalanine.

10. A compound according to claim 5 which is N-[N-[5-[4-(aminoiminomethyl)phenyl]-1-oxo-4E-pentenyl]-L-α-aspartyl]-L-phenylalanine.

11. A compound according to claim 5 which is N-[N-[5-[4-(aminoiminomethyl)phenyl]-1-oxo-4Z-pentenyl]-L-α-aspartyl]-L-phenylalanine.

12. A compound according to claim 5 which is N-[N-[5-[4-(aminoiminomethyl)phenyl]-1-oxopentyl]-L-α-aspartyl]-N-methyl-L-phenylalanine.

13. A compound according to claim 5 which is N-[N-[5-[4-(aminoiminomethyl)phenyl]-1,4-dioxopentyl]-L-α-aspartyl]-L-phenylalanine.

14. A compound according to claim 5 which is N-[N-[6-[4-(aminoiminomethyl)phenyl]-1-oxohexyl]-L-α-aspartyl]-L-phenylalanine.

15. A compound according to claim 5 which is N-[N-[5-[4-(aminoiminomethyl)phenyl]-4-hydroxy-1-oxopentyl]-L-α-aspartyl]-L-phenylalanine.

16. A compound according to claim 5 which is N-[N-[6-[3-(aminoiminomethyl)phenyl]-1-oxo-5Z-hexenyl]-L-α-aspartyl]-L-phenylalanine.

17. A compound according to claim 5 which is N-[N-[4-[4-(aminoiminomethyl)phenyl]-1-oxobutyl]-L-α-aspartyl]-L-phenylalanine.

18. A compound according to claim 5 which is N-[N-[5-[4-(aminoiminomethyl)phenyl]-1-oxopentyl]-L-α-aspartyl]-L-phenylalanine, monohydrochloride.

19. A compound according to claim 5 which is N-[N-[6-[4-(aminoiminomethyl)phenyl]-1-oxohexyl]-L-α-aspartyl]-L-phenylalanine.

20. A compound according to claim 2 wherein Z is hydrido.

21. A compound according to claim 20 which is 3S-[[5-[4-(aminoiminomethyl)phenyl]-1-oxopentyl]amino]-4-oxo-4-[(2-phenylethyl)amino]butanoic acid, acetate salt.

22. A compound according to claim 20 which is 3S-[[5-[4-(aminoiminomethyl)phenyl]-1-oxopentyl]amino]-4-[[2-(4-methoxyphenyl)ethyl]amino]-4-oxobutanoic acid.

23. A compound according to claim 1 of the formula

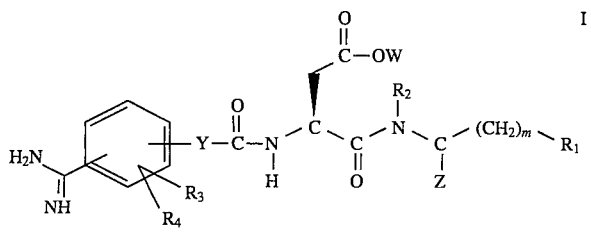

or a pharmaceutically acceptable salt thereof, wherein

R₁ is alkyl having 1 to 6 carbon atoms wherein said alkyl may be substituted by alkyl having 1 to 4 carbon atoms;

R₂ is hydrido or alkyl having 1 to 6 carbon atoms;

R₃ and R₄ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

24. A compound according to claim 23 which is 3S-[[5-[4-(aminoiminomethyl)phenyl]-1-oxopentyl]amino]-4-[(2-methylpropyl)amino]-4-oxobutanoic acid.

25. A compound according to claim 23 which is N-[N-[5-[4-(aminoiminomethyl)phenyl]-1-oxopentyl]-L-α-aspartyl]-L-valine.

26. A compound according to claim 1 of the formula

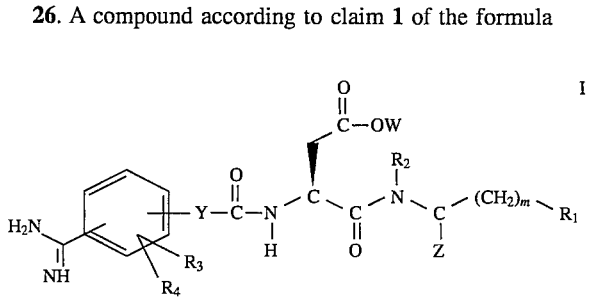

or a pharmaceutically acceptable salt thereof, wherein

R₁ is carboxyl;

R₂ is hydrido; alkyl having 1 to 6 carbon atoms; phenyl; phenylalkyl wherein the alkyl is 1 to 6 carbon atoms and wherein the phenyl ring may be independently substituted one or more times by a substituent selected from alkyl having 1 to 6 carbon atoms, halo, and alkoxy having 1 to 6 carbon atoms;

R₃ and R₄ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxycarbonyl having 1 to 6 carbon atoms; and m is an integer from 0 to 4.

27. A compound according to claim 26 which is 3S-[[5-[4-(aminoiminomethyl)phenyl]-1-oxopentyl]amino]-4-[(2-carboxyethyl)(phenylmethyl)amino]-4-oxobutanoic acid.

28. A compound according to claim 26 which is 3S-[[5-[4-(aminoiminomethyl)phenyl]-1-oxopentyl]amino]-4-[(2-carboxyethyl)(2-phenylethyl)amino]-4-oxobutanoic acid.

29. A compound according to claim 26 which is 3S-[[5-[4-(aminoiminomethyl)phenyl]-1-oxopentyl]amino]-4-[(2-carboxyethyl)[2-(4-methoxyphenyl)ethyl]amino]- 4-oxobutanoic acid.

30. A compound according to claim 26 which is 3S-[[5-[4-(aminoiminomethyl)phenyl]-1-oxopentyl]amino]-4-[(2-carboxyethyl)(2-methylpropyl)amino]-4-oxobutanoic acid.

31. A compound according to claim 1 which is 3S-[[5-[4-(aminoiminomethyl)phenyl]-1-oxopentyl]amino]-4-[2-(1H-indol-3-yl) ethyl]amino]-4-oxobutanoic acid.

32. A compound according to claim 1 which is N-[N-[2-[[3-[4-(aminoiminomethyl)phenyl]-1-oxopropyl] methylamino]-1-oxoethyl]-L-α-aspartyl]-L-phenylalanine.

33. A compound according to claim 1 which is R-[[[[2S-[4-(aminoiminomethyl)phenyl]-1-oxopentyl]amino]-3-carboxy-1-oxopropyl]amino]benzenepentanoic acid.

34. A compound which is N-[N-[2-[[6-(aminoiminomethyl)-2-napthalenyl]oxy]-1-oxoethyl]-L-α-aspartyl]-L-phenylalanine.

35. A compound which is N-[N-[3-[6-(aminoiminomethyl)-2-napthalenyl]-1-oxopropyl]-L-α-aspartyl]-L-phenylalanine.

36. A pharmaceutical composition useful for inhibiting platelet aggregation comprising an effective amount of at least one compound according to claim 1, together with one or more non-toxic pharmaceutically acceptable carriers.

37. A pharmaceutical composition according to claim 36 wherein the compound has the formula

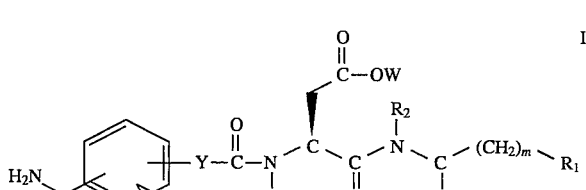

or a pharmaceutically acceptable salt thereof, wherein

R₁ is selected from phenyl or substituted phenyl wherein each substituent can be selected from the group consisting of alkyl having 1 to 6 carbon atoms, halo, alkoxy having 1 to 6 carbon atoms, trifluoromethyl, hydroxy and carboxyl;

R₂ is hydrido or alkyl having 1 to 6 carbon atoms;

R₃ and R₄ are each independently selected from the group consisting of hydrido, alkyl having 1 to 6 carbon atoms, hydroxy, alkoxy having 1 to 6 carbon atoms and halo;

W is hydrido or alkyl having 1 to 6 carbon atoms;

Y is alkyl having 1 to 6 carbon atoms wherein said alkyl may be substituted one or more times by a substituent independently selected from alkyl having 1 to 6 carbon atoms, hydroxy and oxo; alkenyl having 2 to 6 carbon atoms or alkynyl having 2 to 6 carbon atoms;

Z is hydrido, carboxyl or alkoxy carbonyl having 1 to 6 carbon atoms; and m is 0 to 4.

38. A pharmaceutical composition according to claim 37 wherein the compound is N-[N-[5-[4-(aminoiminomethyl)phenyl- 1-oxopentyl]-L-α-aspartyl] -L-phenylalanine.

39. A pharmaceutical composition according to claim 37 wherein the compound is N-[5-[4-(aminoiminomethyl)phenyl] -1-oxo-4-pentynyl]-N-L-α-aspartyl-L-phenylalanine.

40. A pharmaceutical composition according to claim 37 wherein the compound is N-[5-[4-(aminoiminomethyl)phenyl- 1-oxo-4E-pentenyl]-N-L-α-aspartyl-L-phenylalanine.

41. The method of treating a mammal to inhibit platelet aggregation comprising administering a therapeutically effective dose of at least one compound of claim 1 to a mammal in need.

42. A method according to claim 41 wherein said compound is N-[N-[5-[4-(aminoiminomethyl)phenyl-1-oxopentyl] -L-α-aspartyl]-L-phenylalanine.

43. A method according to claim 41 wherein said compound is N-[5-[4-(aminoiminomethyl)phenyl]-1-oxo-4-pentynyl] -N-L-α-aspartyl-L-phenylalanine.

44. A method according to claim 41 wherein said compound is N-[5-[4-(aminoiminomethyl)phenyl]-1-oxo-4E-pentenyl] -N-L-α-aspartyl-L-phenylalanine.

* * * * *